(12) United States Patent
Wittrup et al.

(10) Patent No.: US 8,349,311 B2
(45) Date of Patent: *Jan. 8, 2013

(54) MUTANT INTERLEUKIN-2 (IL-2) POLYPEPTIDES

(75) Inventors: Karl Dane Wittrup, Chestnut Hill, MA (US); Balaji M. Rao, Cambridge, MA (US); Douglas A. Lauffenburger, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/088,045

(22) Filed: Apr. 15, 2011

(65) Prior Publication Data
US 2011/0306752 A1 Dec. 15, 2011

Related U.S. Application Data

(60) Continuation of application No. 12/535,083, filed on Aug. 4, 2009, now Pat. No. 7,951,360, which is a division of application No. 10/894,833, filed on Jul. 19, 2004, now Pat. No. 7,569,215.

(60) Provisional application No. 60/488,537, filed on Jul. 18, 2003.

(51) Int. Cl.
*A61K 38/20* (2006.01)
*C07K 14/55* (2006.01)

(52) U.S. Cl. .................. 424/85.2; 530/351; 530/402

(58) Field of Classification Search .................. None
See application file for complete search history.

(56) References Cited

U.S. PATENT DOCUMENTS

| 4,853,332 A | 8/1989 | Mark et al. |
| 5,116,964 A | 5/1992 | Capon et al. |
| 6,451,308 B1 | 9/2002 | Strom et al. |
| 6,617,135 B1 | 9/2003 | Gillies et al. |

FOREIGN PATENT DOCUMENTS
WO WO 99/60128 11/1999

OTHER PUBLICATIONS

Wang et al., "The Importance of Amino Acid Residues 62 and 126 to the Biological Function of Interlukin-2," Acta Biochimica et Biophysica Sinica, vol. 25(5):558-560 (Sep. 1993).
Mikayama et al., Proct. Natl. Acad. Sci. USA vol. 90, pp. 10056-10060, (1993).
Voet et al., Biochemistry John Wiley & Sons, Inc., pp. 126-128 and 228-234, (1990).
Arima et al., "Pseudo-High Affinity Interleukin 2 (IL-2) Receptor Lacks the Third Component That is Essential for Functional IL-2 Binding and Signaling" *J. Exp. Med.* 176:1265-1272 (1992 ).
Atkins et al., "High-Dose Recombinant Interleukin 2 Therapy for Patients with Metastic Melanoma: Analysis of 270 Patients Treated Between 1985 and 1993" *J. Clin. Oncol.* 17(7):2105-2116 (1999).
Bamborough et al., "The interleukin-2 and interleukin-4 receptors studied by molecular modelling" *Structure* 2:839-851 (1994).
Berndt et al., "Mutagenic Analysis of a Receptor Contact Site on Interleukin-2: Preparation of an IL-2 Analog with Increased Potency" *Biochemistry* 33:6571-6577 (994).
Blanar et al., "Interaction Cloning: Identification of a Helix-Loop—Helix Zipper Protein That Interacts With c-Fos" *Science* 256:1014-1018 (1992).
Boder et al., "Yeast Surface Display for Directed Evolution of Protein Expression, Affinity, and Stability" *Methods Enzymol.* 328:430-444 (2000).
Boder et al., "Yeast surface display for screening combinatorial polypeptide libraries" *Nat. Biotechnol.* 15:553-557 (1997).
Brekke et al., "Structure-Function Relationships of Human IgG" *The Immunologist* 2:125-130 (1994).
Buchli et al., "The Functional Display of Interleukin-2 on Filamentous Phage" *Arch. Biochem. Biophys.* 339:79-84 (1997).
Dubois et al., "IL-15Rα Recycles and Presents IL-15 in *trans* to Neighboring Cells" *Immunity* 17:537-547 (2002).
Dudley et al., "Cancer Regression and Autoimmunity in Patients After Clonal Repopulation with Antitumor Lymphocytes" *Science* 298:850-854 (2002).
Eicher et al., "IL-2Rα on One Cell Can Present IL-2 to IL-2Rβ/$\gamma_c$ on Mother Cell to Augment IL-2 Signaling" *J. of Immunol.* 161(10):5430-5437 (1998).
Fallon et al., "Increased Endosomal Sorting of Ligand to Recycling Enhances Potency of an Interleukin-2 Analog"*J. Biol Chem.* 275(10):6790-6797 (2000).
Fehniger et al., "Interleukin 15: biology and relevance to human disease" *Blood* 97(1):14-32 (2001).
Fyfe et al., "Results of Treatment of 255 Patients With Metastatic Renal Cell Carcinoma Who Received High-Dose Recombinant Interleukin-2 Therapy" *J. Clin. Oncol.* 13:688-696 (1995).
Guthridge et al., "Mechanism of Activation of the GM-CSF, IL-3, and IL-5 Family of Receptors" *Stem Cells* 16:310-313 (1998).
Hémar et al., "Endocytosis of Interleukin 2 Receptors in Human T Lymphocytes: Distinct Intracellular Localization and Fate of the Receptor α, β, and γ Chains" *J. Cell Biol.* 129(1):55-64 (1995).
Hori et al., "Establishment of an Interleukin 2-Dependent Human T Cell Line From a Patient With T Cell Chronic Lymphocytic Leukemia Who is Not Infected With Human T Cell Leukemia / Lymphoma Virus" *Blood* 70:1069-1072 (1987).
Jacobson et al., "Rational interleukin 2 therapy for HIV positive individuals: Daily low doses enhance immune function without toxicity" *Proc. Natl. Acad. Sci. USA* 93:10405-10410 (1996).
Konrad et al., "Pharmacokinetics of Recombinant Interleukin 2 in Humans" *Cancer Res.* 50:2009-2017 (1990).
LeClair et al., "The p50 subunit of NF-κB associates with the NF-IL6 transcription factor" *Proc. Natl. Acad. Sci. USA* 89:8145-8149 (1992).
Liparoto et al., "Analysis of the Role of the Interleukin-2 Receptor γ Chain in Ligand Binding" *Biochemistry* 41:2543-2551 (2002).

(Continued)

Primary Examiner — Prema Mertz
(74) Attorney, Agent, or Firm — Nelson Mullins Riley & Scarborough LLP; Amy E. Mandragouras, Esq.; Christopher L. Frank

(57) ABSTRACT

The present invention relates to IL-2 mutants with increased affinity for the IL-2 alpha-receptor subunit (IL-2Rα). The invention thus includes IL-2 mutants with improved biological potency. The invention also includes methods for directed evolution of IL-2α using yeast surface display to generate mutants with increased affinity for IL-2Rα.

21 Claims, 22 Drawing Sheets

OTHER PUBLICATIONS

Lowman et al., "Selecting High-Affinity Binding Proteins by Monovalent Phage Display" *Biochemistry* 30:10832-10838 (1991).

Morrison et al., "Structural Determinants of Human IgG Function" *The Immunologist* 2:119-124 (1994).

Nelson et al., "Biology of the Interleukin-2 Receptor" *Adv. Immunol.* 70:1-81 (1998).

Parmley et al., "Antibody-selectable filamentous fd phage vectors: affinity purification of target genes" *Gene* 73:305-318 (1988).

Rao et al., "Interleukin-2 mutants with enhanced α-receptor subunit binding affinity" *Protein Engineering* 16(2):1081-1087 (2003).

Raymond et al., "General Method for Plasmid Construction Using Homologous Recombination" *BioTechniques* 26:134-141 (1999).

Saggio et al., "CNTF variants with increased biological potency and receptor selectivity define a functional site of receptor interaction" *EMBO J.* 14:3045-3054 (1995).

Shanafelt et al., "A T-cell-selective interleukin 2 mutein exhibits potent antitumor activity and is well tolerated in vivo" *Nature Biotechnol.* 18:1197-202 (2000).

Smith "Cell Growth Signal Transduction is Quantal" *Receptor Activation by Antigens, Cytokines, Hormones and Growth Factors* 766:263-271 (1995).

Smith, "The Interleukin 2 Receptor" *Annu. Rev. Cell Biol.* 5:397-425 (1989).

Smith, "Lowest Dose Interleukin-2 Immunotherapy" *Blood* 81(6):1414-1423 (1993).

Teshigawara et al., "Interleukin 2 High-Affinity Receptor Expression Requires Two Distinct Binding Proteins" *J. Exp. Med.* 165:223-238 (1987).

Thèze et al., "Interleukin 2 and its receptors: recent advances and new immunological functions" *Immunol. Today* 17:481-486 (1996).

Toniatti et al., "Engineering human interleukin-6 to obtain variants with strongly enhanced bioactivity" *EMBO J.* 15(11):2726-2737 (1996).

Voss et al., "Characterization of the Interleukin 2 Receptors (IL-2R) Expressed on Human Natural Killer Cells Activated In Vivo by IL-2: Association of the p64 Il-2R γ Chain with the IL-2R β Chain in Functional Intermediate-Affinity IL-2R" *J. Exp. Med.* 176:531-541 (1992).

Waldmann et al., "Contrasting Roles of IL-2 and IL-15 in the Life and Death of Lymphocytes: Implications for Immunotherapy" *Immunity* 14:105-110 (2001).

Wu et al., "Solution assembly of the pseudo-high affinity and intermediate affinity interleukin-2 receptor complexes" *Protein Sci.* 8:482-489 (1999).

Zaccolo et al., "An Approach to Random Mutagenesis of DNA Using Mixtures of Triphosphate Derivatives of Nucleoside Analogues" *J. Mol. Biol.* 255:589-603 (1996).

Zaccolo et al., "The Effect of High-frequency Random Mutagenesis on in Vitro Protein Evolution: A Study of TEM-1 β-Lactamase" *J. Mol. Biol.* 285:775-783 (1999).

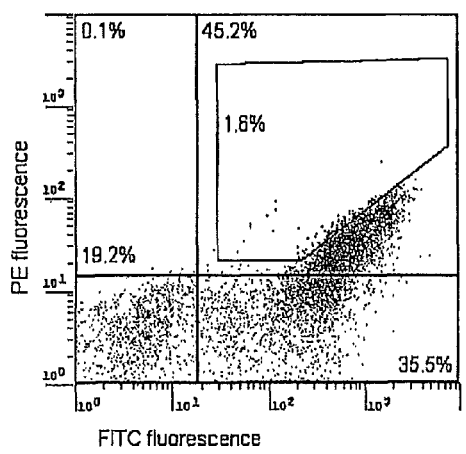 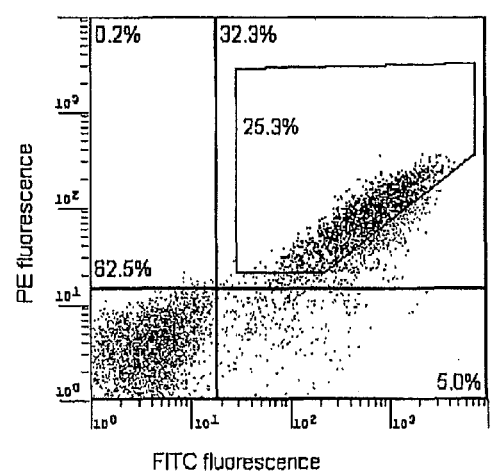
Figure 2A                     Figure 2B

Figure 10A

```
MYRMQLLSCI  ALSLALVTNS  APTSSSTKKT  QLQLEHLLLD  LQMILNGINN
|           |           |           |           |
-20         -10         1           11          21

YKNPKLTRML  TFKFYMPKKA  TELKHLQCLE  EELKPLEEVL  NLAQSKNFHL
|           |           |           |           |
31          41          51          61          71

RPRDLISNIN  VIVLELKGSE  TTFMCEYADE  TATIVEFLNR  WITFCQSIIS
|           |           |           |           |
81          91          101         111         121

TLT
|
131
```

Residues −20-133 correspond to SEQ ID NO:1
Residues 1-133 correspond to SEQ ID NO:2

Figure 10B

```
                        PTSSSTKKT   QLQLEHLLLD  LQMILNGINN
                        |           |           |
                        1           11          21

YKNPKLTRML  TFKFYMPKKA  TELKHLQCLE  EELKPLEEVL  NLAQSKNFHL
|           |           |           |           |
31          41          51          61          71
RPRDLISNIN  VIVLELKGSE  TTFMCEYADE  TATIVEFLNR  WITFSQSIIS
|           |           |           |           |
81          91          101         111         121
TLT  (SEQ ID NO:3)
|
131
```

Figure 11A

| | #mutations | isolates | 1 | 4 | 8 | 9 | 10 | 11 | 13 | 15 | 26 | 29 | 30 | 31 | 35 | 37 | 46 | 48 | 49 | 54 | 61 | 64 |
|---|---|---|---|---|---|---|---|---|---|---|---|---|---|---|---|---|---|---|---|---|---|---|
| Ct25S | | | A | S | K | K | T | Q | Q | E | N | N | N | Y | K | T | M | K | K | K | E | K |
| Mutants from libraries with one round of mutation (from WT) | | | | | | | | | | | | | | | | | | | | | | |
| M13 | 1 | 3 | | | | | | | | | | | | | | | | | | | | |
| N31610_15_ | 2 | 2 | | | | | | | | | | | | | | | | | | | | |
| M12 | 3 | 7 | | | | | | | | | | | | | | | | | | | | R |
| M9 | 3 | 4 | | | | | | | | | | | | | | | | | | | | |
| M6 | 3 | 4 | | | | | | | | | | | | | | | | | | | | |
| M5 | 4 | 1 | | | | | | | | | | | | | | | | | | | | |
| N31610_12_ | 4 | 1 | | | | | | | | | | | D | | | | | | | | | |
| N31610_17_ | 4 | 1 | | | | | | | | | | | | | | | | | E | | | |
| N31610_20_ | 4 | 1 | | | | | | | | | | | S | | | | | | | | | |
| N31610_23_ | 4 | 1 | | | | | | | | | | | | | | | | | | | | |
| N31610_25_ | 4 | 1 | | | | | | | | | | | S | | | | | | | | | |
| N31610_13_ | 5 | 1 | | | | | T | R | | | | | | | R | | | | | | | |
| M16 | 6 | 1 | T | | | | | | | | | | | | | | L | | R | | D | |
| M30 | 6 | 1 | | | | | | | | | | | | | | | | E | | | | |
| N31610_18_ | 7 | 1 | | P | | | A | R | | | | | | | | | | | | | | |
| N31610_11_ | 8 | 1 | | | | | | | | K | | | S | H | R | | | E | | | | |
| Mutants from libraries with two rounds of mutation | | | | | | | | | | | | | | | | | | | | | | |
| N31610_01_ | 8 | 3 | | | | | | | | | | | S | | | | | | | | | |
| N31610_09_ | 8 | 2 | | | | | | | | | | | S | C | | A | | | | | | |
| N31618_04_ | 8 | 1 | | | | | | | | D | S | S | | | | | | | | R | | |
| N31618_08_ | 9 | 5 | | | R | | | R | | D | | | T | | R | R | | | | | | |
| N31618_14_ | 10 | 1 | | | | | | | | | | S | | H | R | A | | E | | | | |

Figure 11B

| | #mutations | isolates | 67 | 68 | 69 | 71 | 73 | 74 | 75 | 76 | 79 | 88 | 89 | 90 | 92 | 99 | 101 | 103 | 114 | 128 | 133 |
|---|---|---|---|---|---|---|---|---|---|---|---|---|---|---|---|---|---|---|---|---|---|
| C125S | | | E | E | V | N | A | Q | S | K | H | N | I | N | I | S | T | F | I | I | T |
| Mutants from libraries with one round of mutation (from WT) | | | | | | | | | | | | | | | | | | | | | |
| M13 | 1 | 3 | | | | A | | | | | | | | | | | | | | | |
| N31610_15 | 2 | 2 | | | | A | | | | P | | | | | | | | | | | |
| M12 | 3 | 7 | | | | A | | | | P | | | | | | | | | | | |
| M9 | 3 | 4 | | | | A | | | | P | | | | | | A | | | | | |
| M6 | 3 | 4 | | | | A | | | | P | | | | | | | | | | T | |
| M5 | 4 | 1 | | | | A | | | | P | | | | | | A | | | | | N |
| N31610_12 | 4 | 1 | | | | A | | | | P | | | | | | | S | | | | |
| N31610_17 | 4 | 1 | | | | A | | V | | | E | | | | | | | | | | |
| N31610_20 | 4 | 1 | | | | A | | | | P | | | | | | | | | | A | |
| N31610_23 | 4 | 1 | | | | A | | | | P | | | D | | | P | | | | | |
| N31610_25 | 4 | 1 | | | | A | | | | P | | | | | | | | | | T | |
| N31610_13 | 5 | 1 | | | | A | | | | P | | | | | | | | | | | |
| M16 | 6 | 1 | | | | A | | | | | R | | | | | | | | | | |
| M30 | 6 | 1 | | D | | T | | | | | | | H | | | | S | V | | | |
| N31610_18 | 7 | 1 | | | | A | | | | P | | | D | | | | | | | | A |
| N31610_11 | 8 | 1 | | | | A | | | | P | | | | | | T | | | | | |
| Mutants from libraries with two rounds of mutation | | | | | | | | | | | | | | | | | | | | | |
| N31610_01 | 8 | 3 | | D | A | A | | P | P | R | | | H | | | | | | | | |
| N31610_09 | 8 | 2 | | | | A | V | P | | R | | | | | | | | | | T | |
| N31618_04 | 8 | 1 | G | | | A | | P | | | | | | | T | | | | | | |
| N31618_08 | 9 | 5 | | | | A | | P | | | | | | | T | | | | | | |
| N31618_14 | 10 | 1 | | | | A | R | P | | | | D | V | | | | | | | | |

Figure 13A
Figure 13B
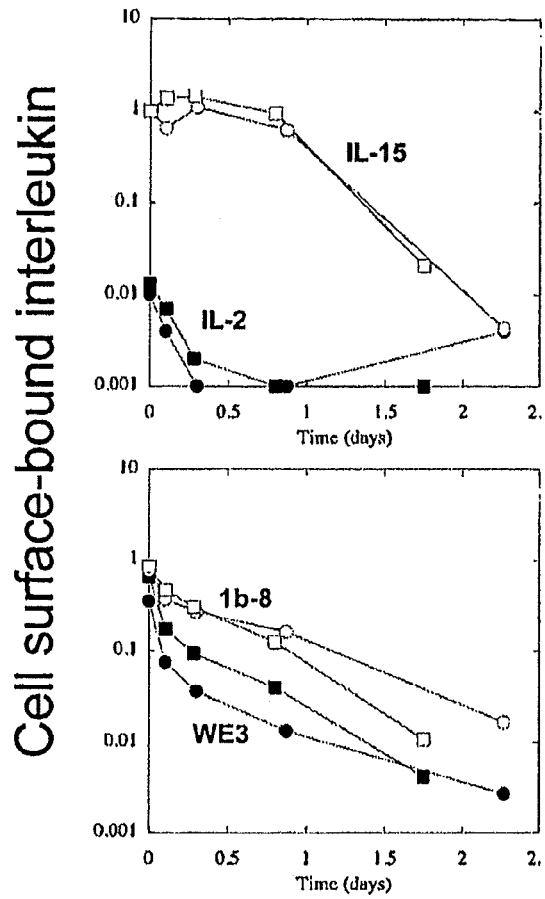
Figure 13C
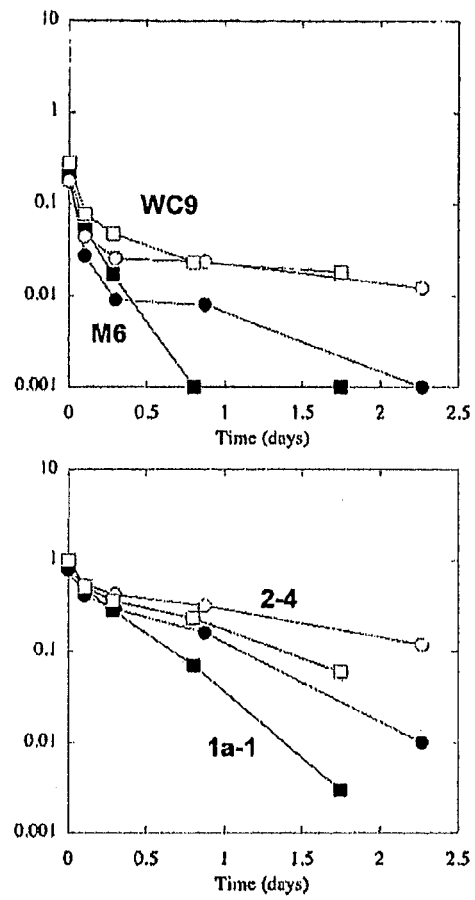
Figure 13D

MUTANT INTERLEUKIN-2 (IL-2) POLYPEPTIDES

CROSS-REFERENCE TO RELATED APPLICATIONS

This application is a continuation of U.S. application Ser. No. 12/535,083, filed Aug. 4, 2009, which is a divisional application of U.S. application Ser. No. 10/894,833, filed Jul. 19, 2004 (now U.S. Pat. No. 7,569,215), which claims the benefit of the priority date of U.S. Application No. 60/488,537, filed Jul. 18, 2003, the contents of which are hereby incorporated by reference in their entireties.

FEDERALLY SPONSORED RESEARCH OR DEVELOPMENT

This invention was made with government support under Grant No. EEC9843342 awarded by the National Science Foundation. The government has certain rights in this invention.

TECHNICAL FIELD

This invention relates to mutant interleukin polypeptides, including mutants of interleukin-2 (IL-2), and related therapeutics, compositions, methods of treatment, and uses.

BACKGROUND

Interleukin-2 (IL-2) is a cytokine that induces proliferation of antigen-activated T cells and stimulates natural kill (NK) cells. The biological activity of IL-2 is mediated through a multi-subunit IL-2 receptor complex (IL-2R) of three polypeptide subunits that span the cell membrane: p55 (IL-2Rα, the alpha subunit), p75 (IL-2Rβ, the beta subunit) and p64 (IL-2Rγ, the gamma subunit). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "*Cell Growth Signal Transduction is Quantal*" In *Receptor Activation by Antigens, Cytokines, Hormones, and Growth Factors* 766:263-271, 1995). The IL-2:IL-2R complex is internalized upon ligand binding and the different components undergo differential sorting. IL-2Rα is recycled to the cell surface, while IL-2 associated with the IL-2:IL-2Rβγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., *Cancer Res.* 50:2009-2017, 1990).

SUMMARY

The present invention is based, in part, on our discovery that IL-2 can be engineered to produce mutants that bind the IL-2R complex generally or the IL-2Rα subunit specifically with an affinity that differs from that of the corresponding wild-type IL-2 or of a presently available mutant (referred to as C125S, as the cysteine residue at position 125 is replaced with a serine residue). There are a variety of ways to describe the altered abilities of our IL-2 mutants. For example, we refer below to an increase in affinity relative to a corresponding wild-type IL-2 molecule or to C125S. We note, for example, that the affinity of our IL-2 mutant for IL-2Rα may increase by, for example, at least about 2%, 5%, 10%, 15%, 20%, 25%, 50%, or more relative to wild-type IL-2 or C125S; or by, for example, 2-, 5-, 10-, 15-, 20-, 25-, 50-fold or more). We may also refer to an increase in the time (or average time) the mutant IL-2 persists on a cell surface or to the rate at which it dissociates from its receptor or a subunit thereof. The mutants may also be characterized in terms of their affinity equilibrium constant ($K_d$). While receptor binding affinities can be measured, and while there are a variety of ways to characterize the altered receptor interaction, the scope of the present invention encompasses mutant IL-2 polypeptides that have the structure described below and that confer a clinical benefit on a patient to whom they are administered that is equivalent to or, preferably, in some way superior to, the benefit the patient would experience following treatment with wild-type IL-2 (represented herein by SEQ ID NO:2) or a corresponding wild-type IL-2 based therapeutic agent (e.g., C125S, commercially available as PROLEUKIN, represented herein by SEQ ID NO:3). In other words, with respect to function, the present IL-2 mutants may have an increased affinity for IL-2R to any degree that is sufficient to improve their utility as IL-2-based therapeutic agents, regardless of the extent of the improvement or the way in which affinity is changed, measured, or described. Potential advantages of the present mutants are described further below.

Accordingly, the present invention features mutant interleukin-2 (IL-2) polypeptides that include an amino acid sequence that is at least 80% identical to SEQ ID NO:2 (e.g., 85, 87, 90, 95, 97, 98, or 99% identical) and that bind an IL-2 receptor α subunit (IL-2Rα) with an affinity that is greater than the affinity with which wild type IL-2 (SEQ ID NO:2) or PROLEUKIN (represented by SEQ ID NO:3) binds the IL-2Rα. The amino acid sequence within mutant IL-2 polypeptides can vary from SEQ ID NO:2 by virtue of containing (or only containing) one or more amino acid substitutions, which may be considered conservative or non-conservative substitutions. Non-naturally occurring amino acids can also be incorporated. Alternatively, or in addition, the amino acid sequence can vary from SEQ ID NO:2 (which may be considered the "reference" sequence) by virtue of containing and addition and/or deletion of one or more amino acid residues. More specifically, the amino acid sequence can differ from that of SEQ ID NO:2 by virtue of a mutation at least one of the following positions of SEQ ID NO:2: 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 (or combinations thereof). As noted, as few as one of these positions may be altered, as may two, three, four, five, six, seven, eight, nine, ten, or 11 or more (including up to all) of the positions. For example, the amino acid sequence can differ from SEQ ID NO:2 at positions 69 and 74 and further at one or more of positions 30, 35, and 128. The amino acid sequence can also differ from SEQ ID NO:2 at one of the following sets of positions: (a) positions 64, 69, and 74; (b) positions 69, 74, and 101; (c) positions 69, 74, and 128; (d) positions 30, 69, 74, and 103; (e) positions 49, 69, 73, and 76; (f) positions 69, 74, 101, and 133; (g) positions 30, 69, 74, and 128; (h) positions 69, 74, 88, and 99; (i) positions 30, 69, 74, and 128; (j) positions 9, 11, 35, 69, and 74; (k) positions 1, 46, 49, 61, 69, and 79; (l) positions 48, 68, 71, 90, 103, and 114; (m) positions 4, 10, 11, 69, 74, 88, and 133; (n) positions 15, 30 31, 35, 48, 69, 74, and 92; (O) positions 30, 68, 69, 71, 74, 75, 76, and 90; (p) positions 30, 31, 37, 69, 73, 74, 79, and 128; (q) positions 26, 29, 30, 54, 67, 69, 74, and 92; (r) positions 8, 13, 26, 30, 35, 37, 69, 74, and 92; and (s) positions 29, 31, 35, 37, 48, 69, 71, 74, 88, and 89. Aside from mutations at these positions, the amino acid sequence of the mutant IL-2 polypeptide can otherwise be identical to SEQ ID NO:2. With respect to specific substitutions, the amino acid sequence can differ from SEQ ID NO:2 by virtue of having one or more of the following mutations: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54E, E61D, K64R, E67G, E68D, V69A, N71T, N71A, N71R, A73V, Q74P, S75P, K76E, K76R, H79R, N88D, I89V, N90H, I92T, S99P, T101A, F103S, I114V, I128T, I128A, T133A, or T133N. Our nomenclature is consistent with that of the scientific literature, where the single letter code of the amino acid in the wild-type or reference sequence is followed by its position within the sequence and then by the single letter code of the amino acid with which it is replaced. Thus, A1T designates a substitution of the alanine residue a position 1 with threonine. Other mutant polypeptides within the scope of the invention include those that include a mutant of SEQ ID NO:2 having substitutions at V69 (e.g. A) and Q74 (e.g., P). For example, the amino acid sequence can include one of the following sets of mutations with respect to SEQ ID NO:2: (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (l) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54E, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V.

As noted above, any of the mutant IL-2 polypeptides we describe can include the sequences described; they can also be limited to the sequences described and otherwise identical to SEQ ID NO:2. Moreover, any of the mutant IL-2 polypeptides we describe can optionally include a substitution of the cysteine residue at position 125 with another residue (e.g., serine) and/or can optionally include a deletion of the alanine residue at position 1 of SEQ ID NO:2.

With respect to affinity, the mutant IL-2 polypeptides of the invention can bind to the IL-2Rα subunit with a $K_d$ of less than about 28 nM (e.g., less than about 25 nM; less than about 5 nM; about 1 nM; less than about 500 pM; or less than about 100 pM). More specifically, a mutant IL-2 polypeptide can have an affinity equilibrium constant less than 1.0 nM (e.g., about 0.8, 0.6, 0.4, or 0.2 nM). Affinity can also be expressed as a relative rate of dissociation from an IL-2Rα subunit or from an IL-2 receptor complex (e.g., a complex expressed on the surface of a cell or otherwise membrane bound). For example, the mutant IL-2 polypeptides can dissociate from, for example, IL-2Rα, at a decreased rate relative to a wild-type polypeptide (e.g., SEQ ID NO:2) or to an IL-2 based therapeutic (e.g., SEQ ID NO:3). Alternatively, affinity can be characterized as the time, or average time, a mutant IL-2 polypeptide persists on, for example, the surface of a cell expressing an IL-2R. For example, a mutant IL-2 polypeptide can persist on the receptor for at least about 2, 5, 10, 50, 100, or 250 times (or more) as long as a wild-type form of the interleukin (e.g., SEQ ID NO:2) or an IL-2-based therapeutic (e.g., SEQ ID NO:3).

Any of the mutant IL-2 polypeptides of the invention can be glycosylated or non-glycosylated and/or phosphorylated or non-phosphorylated.

The mutant IL-2 polypeptides can also include, joined either to the N-terminus, the C-terminus, or both (a) heterologous amino acid sequence(s) that can increase the circulating half-life of the mutant IL-2 polypeptide, enhance expression of the mutant IL-2 polypeptide, direct cellular localization of the mutant IL-2 polypeptide, or serve as a marker or tag. For example, the mutant IL-2 polypeptide can be an Fc region of an immunoglobulin (or a fragment thereof that is sufficient to increase the circulating half-life of the mutant IL-2 polypeptide to which it is fused), a FLAG epitope, a c-myc epitope, albumin (or a fragment thereof), an albumin-binding peptide, or an Aga2p agglutinin polypeptide. The heterologous amino acid sequence can also be, or can include, a toxin or the sequence of an antibody (e.g., a single chain antibody) or an antigen-binding fragment thereof.

Compositions, including physiologically acceptable compositions, that contain a mutant IL-2 polypeptide (any described herein as within the scope of the present invention or as featured in the present invention) are also within the scope of the present invention and are described further below. We note here that any formulation suitable for a presently known IL-2-based therapeutic agent (e.g., SEQ ID NO:3) is suitable for use in administering the present IL-2 mutants. For example, a mutant IL-2 polypeptide of the invention can be supplied in a lyophilized form and reconstituted with sterile water for injection, with mannitol, sodium dodecyl sulfate (SDS), and a buffer such as monobasic and/or dibasic sodium phosphate. Antibiotics, preservatives, and other agents (such as anti-caking agents) may be included if desired.

Nucleic acid molecules that encode any of the mutant IL-2 polypeptides of the invention are also within the scope of the invention. The nucleic acids are useful, for example, in making the polypeptides of the present invention and as therapeutic agents. They may be administered to cells in culture or in vivo and may include a secretory signal that directs or facilitates secretion of the mutant IL-2 polypeptide from the cell. Also within the scope of the invention are expression vectors and host cells that contain or include nucleic acids of the invention (described further below). While we may refer to the nucleic acids as "isolated," we note that, by definition, the mutant IL-2 polypeptides of the invention are not wild-type polypeptides and, as such, would not be encoded by naturally occurring nucleic acids. Thus, while the polypeptides and nucleic acids of the present invention may be "purified," "substantially purified," or "isolated," they need not be so in order to be distinguished from naturally occurring materials.

In other embodiments, the invention features methods for identifying mutant IL-2 polypeptides that bind to the IL-2Rα subunit with an affinity greater than that of wild-type IL-2 (SEQ ID NO:2) or of the polypeptide of SEQ ID NO:3. These methods can be carried out using a library of nucleic acids that include sequences encoding a plurality of mutant IL-2 polypeptides (the libraries may be made as described in our studies below and may contain fewer or more clones than we obtained). Once obtained, the nucleic acids can be expressed in a population of cells (including mammalian, bacterial, or yeast cells) such that the plurality of mutant IL-2 polypeptides are expressed on the surfaces of cells within the population. Once expressed, one can evaluate the binding of the mutant to one or more subunits of IL-2R (including IL-2Rα) or to a receptor complex as a whole. Binding can be evaluated and characterized in any of the ways described herein (e.g., by affinity binding constant, persistence, dissociation rate, etc.).

Mutants of interest can then be identified by identifying the clones (nucleic acid sequences) encoding the IL-2 polypeptides with desirable affinity (e.g. affinity greater than that exhibited by SEQ ID NO:2 or SEQ ID NO:3, which can be included in comparable binding studies for comparison). Mutant IL-2 polypeptides and nucleic acids identified by the methods just described are also within the scope of the present invention.

In other embodiments, the invention features methods of treating a patient (e.g., a human patient) who has cancer or a viral infection. The methods include administering, to the patent, a therapeutically effective amount of one or more of the mutant TL-2 polypeptides of the invention. The methods of the invention can be carried out with any of the polypeptides of the invention; one of ordinary skill in the art would understand our teaching that the methods can be practiced with any of the polypeptides that exhibit a certain degree of identity to SEQ ID NO:2 or SEQ ID NO:3 and an improved affinity for their receptor and would not expect a full repeat of our description of those polypeptides here. Prior to administration, one can identify a patient in need of treatment. While routes of administration are described further below, we note that the administration can be via a parenteral route (e.g., into a blood vessel (e.g., intravenous), through the peritoneum (e.g., intraperitoneal), or beneath the skin (e.g., subcutaneous)). Similarly, while patients amenable to treatment are described further below, we note here that the patient may be one who is diagnosed as having a renal carcinoma or a melanoma. The patient may also be infected with a virus such as an influenza virus, a herpes virus, a papilloma virus, or a human immunodeficiency virus (HIV, including HIV-1 or HIV-2, and may be referred to as "HIV-positive"). The methods of treatment can also include ex vivo treatment of cells obtained from a patient. For example, the invention encompasses a method of treating a patient who has cancer or a viral infection (as above) by obtaining a population of cells, from the patient, that includes T cells (also referred to as T lymphocytes). One can then contact the population of cells with any given mutant IL-2 polypeptide (any mutant IL-2 polypeptide of the invention) to generate a population of modified cells, which can then be returned to the patient in sufficient number to treat the patient. Here too, one can identify a patient in need of treatment before the treatment begins. The patient's cells may be treated ex vivo, as described, and the patient may, in addition, be given a mutant IL-2 polypeptide, as described. The polypeptide can be administered before, at about the same time as, or after their T cells are harvested and/or re-administered. The methods of the present invention can be carried out, if necessary or desired, together with conventional methods of treatment a patient for cancer or a viral disease (e.g., while administering a chemotherapeutic agent, delivering radiation therapy, in conjunction with a surgical procedure (e.g., following a biopsy or surgical procedure to remove a tumor or other cancerous growth) or during the course of an anti-viral therapy).

While dosages are also discussed further below, the mutant IL-2 polypeptides of the invention are, due to their improved affinity for their receptor, expected to stimulate longer-term expansion of lymphocytes. It should, therefore, be possible to administer a smaller dosage or the same dosage less frequently than has been used with IL-2-based therapeutics to date. We further expect the mutant IL-2 polypeptides of the invention to produce less NK cell stimulation and, therefore, lessen the toxic side effects that may be associated with IL-2-based therapeutics. In addition, because the mutant polypeptides can contain a relatively small number of mutant amino acid residues, we expect they will not be immunogenic or will not induce a great immune response.

Treatment with wild-type IL-2 can lead to activation-induced cell death (AICD), while treatment with interleukin-15 (IL-15 (*Nature Med.* 7:114-118, 2001) inhibits AICD and promotes CD8$^+$ memory cell persistence (*J. Clin. Immunol.* 22:51, 2002). We believed this distinction was due to the difference in affinity of IL-2 and IL-15 for their private alpha receptors (they both signal through the same β and γ receptor subunits). However, as the IL-15Rα subunit is expressed in more tissue types than IL-2Rα (*J. Biol. Chem.* 270:29862-29869, 1995), treatment with IL-15 and IL-2 would be expected to affect different, but overlapping, populations of cells. We believed that a mutant of IL-2 with enhanced affinity for its alpha receptor subunit would send persistent growth signals, reminiscent of those sent by IL-15. Such mutant IL-2 polypeptides would better stimulate activated T cells and consequently enhance the efficacy of the cytotoxic T cells/lymphocytes (CTLs) attack of cancerous or virally-infected cells.

The invention further features other (i.e., non-IL-2) mutant cytokines that exhibit a decreased dissociation rate from a receptor subunit, such that signaling from the receptor/ligand complex persists for a longer time period (in culture or in vivo) following exposure (e.g., transient exposure) to the mutant cytokine. More specifically, the mutant cytokines can be mutants of GM-CSF, IL-3, IL-5, IL-6 or IL-15 (e.g., mutants that are at least 80% identical (e.g., at least 87, 90, 98, 98, or 99% identical) to their wild-type counterparts, as described herein with reference to IL-2) that bind their cognate receptors with an affinity greater than the corresponding wild-type cytokine. The cytokines disclosed here all signal through receptors having non-signaling alpha capture receptor subunits that would function analogously to IL-2Rα (see Guthridge et al., *Stem Cells* 16:310-313, 1998).

All publications, patent applications, patents, and other references mentioned herein are incorporated by reference in their entirety.

Although methods and materials similar or equivalent to those described herein can be used in the practice or testing of the present invention, suitable methods and materials are described below. Other features and advantages of the invention will be apparent from the following detailed description, and from the claims.

DESCRIPTION OF THE DRAWINGS

FIGS. 2A-2B are tracings that illustrate an ensemble of clones (FIG. 2B) that exhibit better binding for IL-2Rα than does C125S (FIG. 2A). Labeling was performed with saturating concentration of anti-HA antibody (12CA5) and 0.4 nM IL-2Rα, at 37° C.

FIGS. 5A, 5B, 5C, and 5D show the results we obtained for C125S, M6, C1, and M1, respectively.

FIG. 6A shows the number of viable KIT225 cells over time, when cultured with different concentrations of C125S. FIGS. 6B-6F provide ratios of the viable cells to non-viable cells when cultured with the mutants M6 (open squares), M1 (open triangles), C1 (open circles) or C125S (crosses). The means are joined by lines: C125S (heavy solid line), M6 (lighter solid line), C1 (dashed line) and M1 (dotted line).

FIGS. 10A-10B are representations of polypeptide sequences. FIG. 10A is a representation of IL-2 from Gen-Bank® (P01585: Interleukin-2 precursor (IL-2) (T cell growth factor) (TCGF) (Aldesleukin) [gi:124325] (SEQ ID NO:1). The C125 residue is underlined. Residues numbered 1-133 correspond to the mature form of human IL-2 (SEQ ID NO:2). FIG. 10B is a representation of an IL-2-based therapeutic that is presently commercially available (PROLEUKIN) (SEQ ID NO:3).

FIGS. 11A-11B represent a Table that illustrates the positions and identity of amino acid substitutions in mutant IL-2 polypeptides with increased affinity for IL-2Rα. FIG. 11A depicts the mutations in residues 1-64 of IL-2, and FIG. 11B depicts the mutations in residues 65-133 of IL-2. N31610_25_ is also referred to as mutant WE3. N31610_18_ is also referred to as mutant WC9. N31610_01_ is also referred to as mutant 1a-1. N31618_08_ is also referred to as mutant 1b-8. N31618_14_ is also referred to as mutant 2-4.

FIGS. 13A-13D are graphs depicting cell surface persistence of IL-2 mutants. F15R-Kit cells expressing IL-2Rα and IL-15Rα were labeled with 100 pM wild-type IL-2, IL-2 mutants or IL-15 for 30 minutes at 37° C. and pH 7.4. Cells were then washed with and resuspended in cytokine-free medium. Cell surface bound protein was measured using flow cytometry at different time points following cytokine withdrawal. Data are normalized by the initial value of cell surface bound 2-4 for wild-type IL-2 and the IL-2 mutants and the initial value of cell surface bound IL-15 for IL-15. Normalized values less than 0.001 are plotted as 0.001. Results for IL-2 and IL-15 are depicted in FIG. 13A. Results for M6 and WC9 are depicted in FIG. 13B. Results for 1b-8 and WE3 are depicted in FIG. 13C. Results for 2-4 and 1a-1 are depicted in FIG. 13D.

FIGS. 17A and 17B depict results for duplicate experiments.

DETAILED DESCRIPTION

Figure 1A:
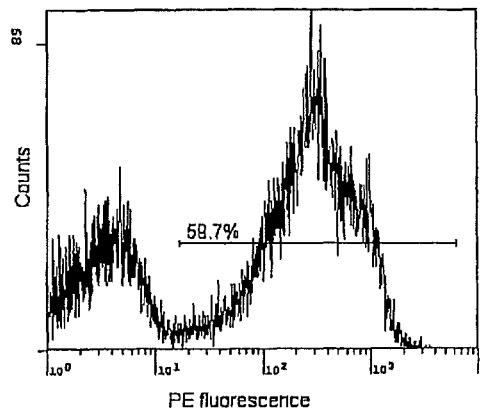
FIGS. 1A-1D are tracings that illustrate specific binding between an Aga2-p-IL-2 fusion with a C-terminal c-myc epitope tag and the soluble ectodomain of IL-2Rα. Yeast cells expressing the fusion were labeled with saturating concentrations of anti-c-myc antibody (mAb 9e10) in the absence (FIG. 1A) and presence (FIG. 1B) of soluble IL-2Rα (52 nM). As a negative control, yeast displaying an irrelevant scFv (D1.3) were also examined in the absence (FIG. 1C) and presence (FIG. 1D) of soluble IL-2Rα.
Figure 1B:
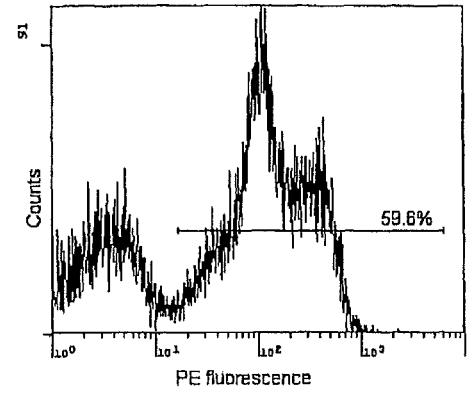
Figure 1C:
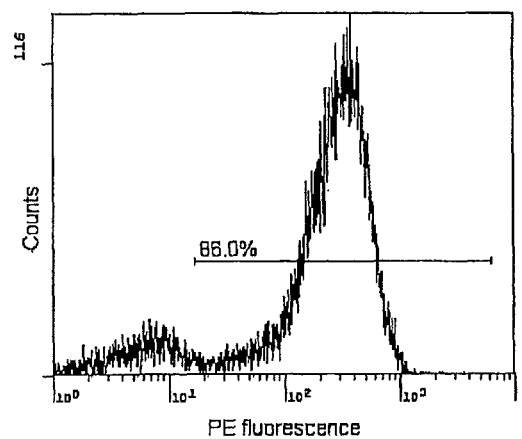
Figure 1D:
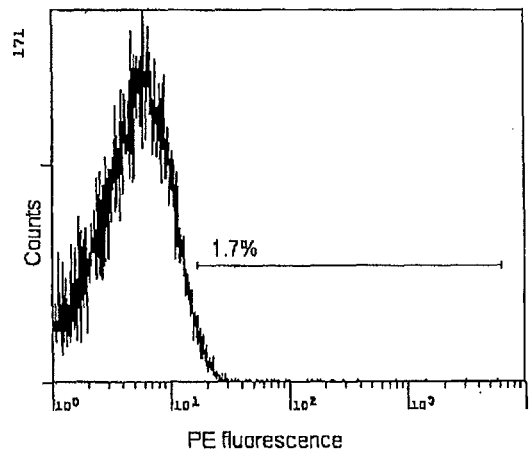
Figure 3:
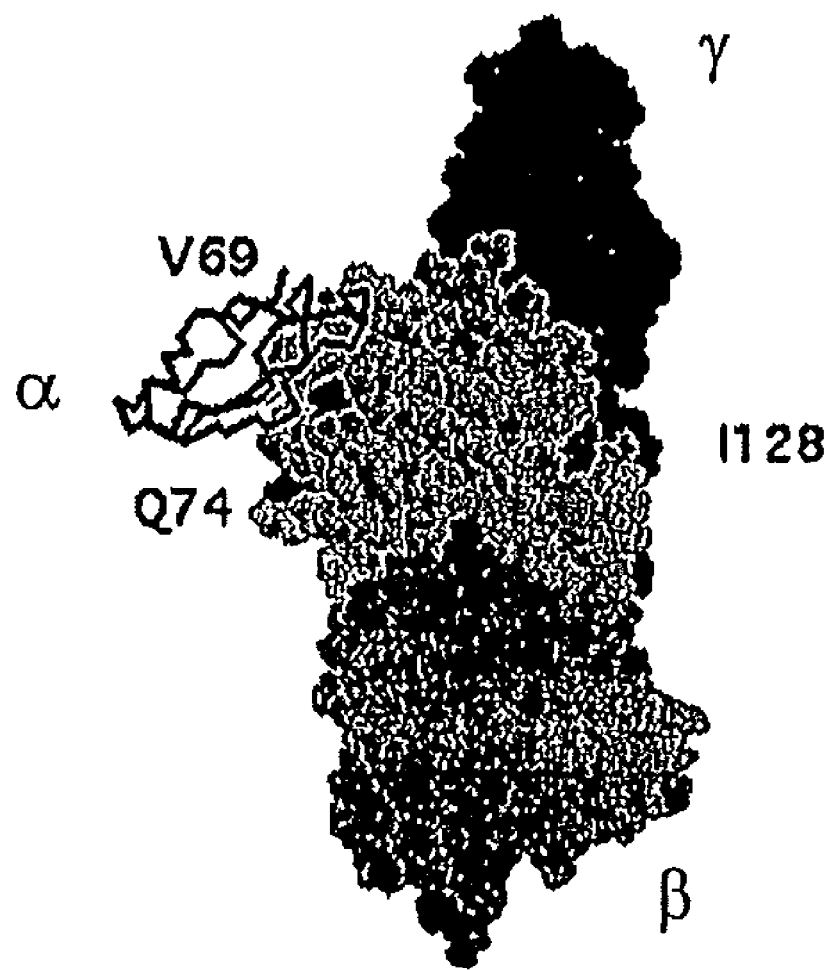
FIG. 3 is a space-filling model. The locations of mutations in IL-2 (at left) are shown on a model of an IL-2 receptor complex (at right; the γ, α-, and β-subunits are marked as such). The residues mutated in a particular IL-2 mutant are also marked (Q74, V69, and I128).
Figure 4:
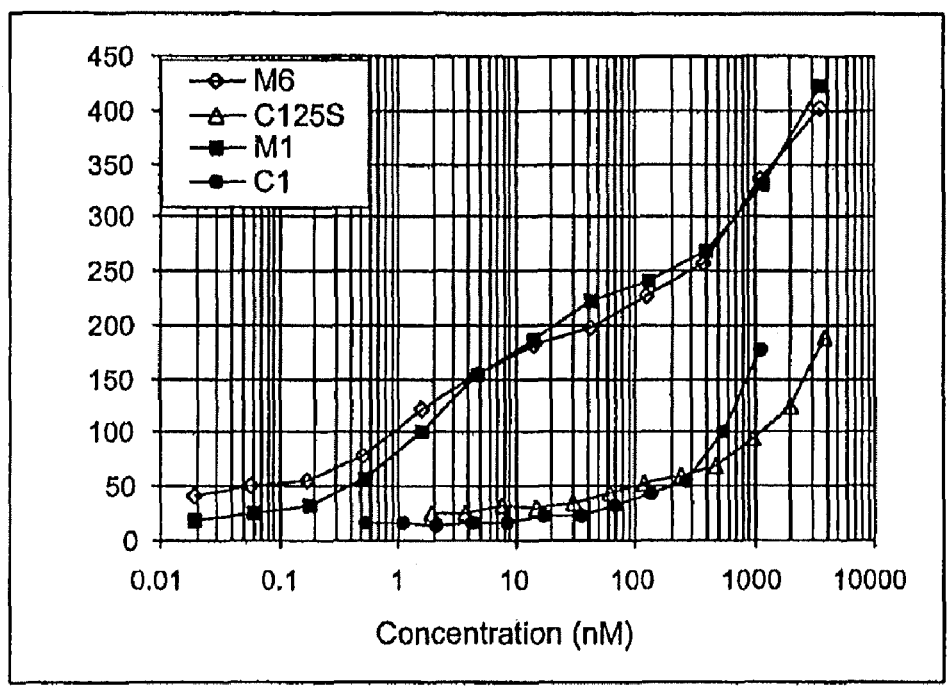
FIG. 4 is an exemplary binding curve illustrating the binding of three IL-2 mutants (M6 (diamonds), M1 (squares), and C1 (circles)) and C125S (triangles) to KIT225 cells, which express an excess of IL-2Rα, at 37° C. The data shown are representative data from at least two experiments for each mutant or for C125S. The binding curves look similar at 4° C.
Figure 5A:
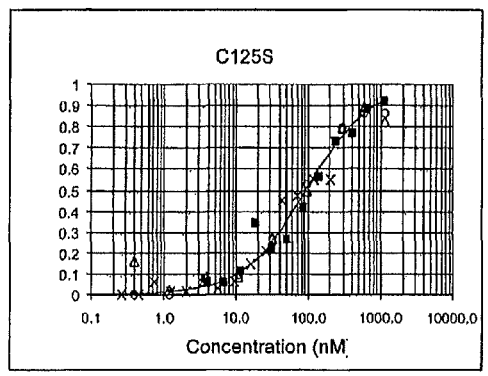
FIGS. 5A-5D are exemplary binding curves illustrating the binding of IL-2 mutants to YT-2C2 cells, which express IL-2Rβ and IL-2Rγ. Different symbols in each curve denote different data sets.
Figure 5B:
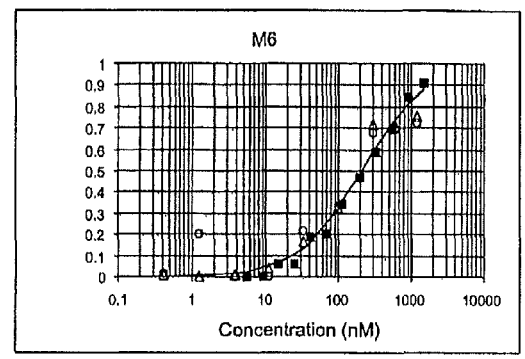
Figure 5C:
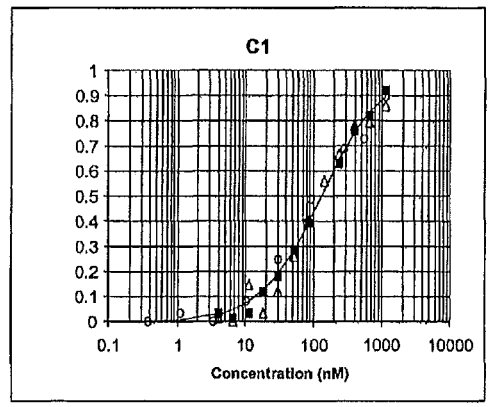
Figure 5D:
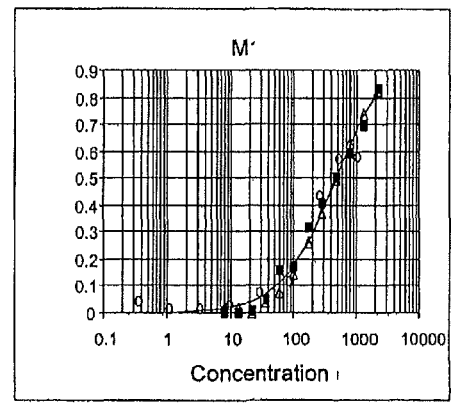
Figure 6A:
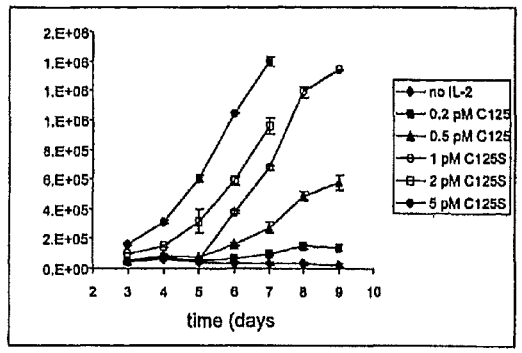
FIGS. 6A-6F are graphs illustrating the proliferation of IL-2 dependent KIT225 cells in response to C125S and the IL-2 mutants M6, M1, and C1 at various concentrations (as indicated on the graphs).
Figure 6B:
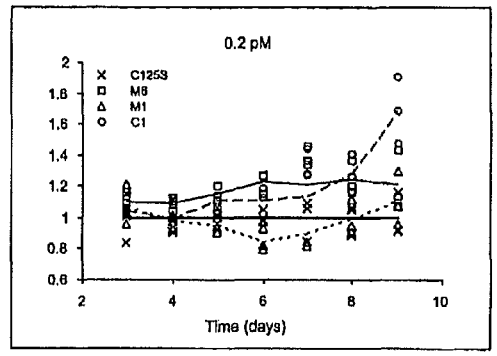
Figure 6C:
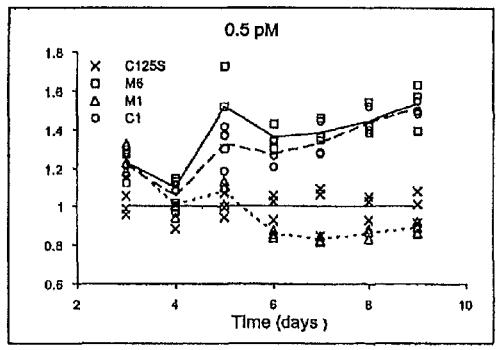
Figure 6D:
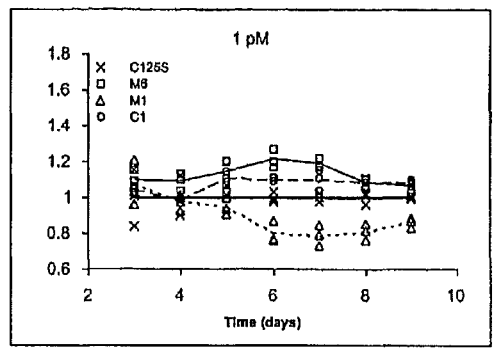
Figure 6E:
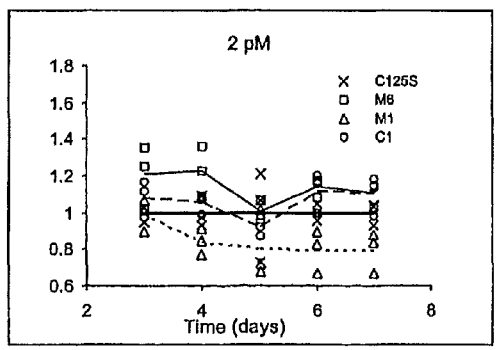
Figure 6F:
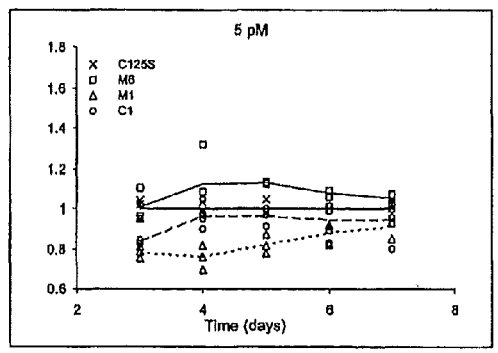

IL-2-based therapeutic have been exploited to stimulate the proliferation of T cells in the course of treatment for metastatic renal carcinoma and melanoma (Atkins et al., *J. Clin. Oncol.* 17:2105-2116, 1999; Fyfe et al., *J. Clin. Oncol.* 13:688-96, 1995). However, a narrow therapeutic window has hampered these therapies. Undesirable inflammatory responses are activated at IL-2 concentrations above 100 pM through stimulation of NK cells (Jacobson et al., *Proc. Natl. Acad. Sci. USA* 93:10405-10, 1996; Smith, *Blood* 93:1414-23, 1993), while stimulation of T cells is not achieved below 1 pM. Given the rapid systemic clearance of IL-2 (an initial clearance phase with a half-life of 12.9 minutes followed by a slower phase with a half-life of 85 minutes (Konrad et al., *Cancer Res.* 50:2009-17, 1990)), it is difficult to maintain therapeutic concentrations of IL-2 (1-100 pM) for a sustained period.

The expression of IL-2Rα is upregulated in antigen-activated T cells (Smith, *Annu. Rev. Cell Biol.* 5:397-425, 1989;

Theze et al., *Immunology Today* 17:481-486, 1996). NK cells in general express only the IL-2Rβ and IL-2Rγ subunits (Voss et al., *J. Exp. Med.* 176:531-541, 1992), so enhanced affinity for IL-2Rα would be expected to increase the specificity of IL-2 for activated T cells relative to NK cells. Manipulation of the binding affinities to these receptor subunits might be used to alter the biological response to IL-2 and potentially create an improved therapeutic. Screening of over 2,600 IL-2 variants created by combinatorial cassette mutagenesis has led to the isolation of an IL-2 variant (L18M, L19S) with increased potency (Berndt et al., *Biochemistry* 33:6571-6577, 1994; this mutant is also referred to as 2D1). 2D1 internalized by receptor-mediated endocytosis is recycled to a greater extent than wild-type IL-2, leading to decreased depletion of 2D1 in cell culture and hence improved biological potency (Fallon et al., *J. Biol. Chem.* 275:6790-6797, 2000). The 2D1 mutant is explicitly excluded from the mutant IL-2 polypeptides of the present invention, as is C125S, as are mutants substituted at positions 20 and 88 and/or 126 of wild-type IL-2 (e.g., mutant IL-2 polypeptides having D20H/I and N88G/I/R mutations).

Site-directed mutagenesis was also utilized to isolate IL-2 variants causing reduced stimulation of NK cells via reduced binding to IL-2Rβ and IL-2Rγ (Shanafelt et al., *Nature Biotechnol.* 18:1197-1202, 2000; this mutant is also referred to as BAY 50-4798 and is also explicitly excluded from the scope of the present invention). Increasing the affinity of IL-2 for IL-2Rα at the cell surface will increase receptor occupancy within a limited range of IL-2 concentration, as well as raise the local concentration of IL-2 at the cell surface.

In part, the invention relates to IL-2 mutants with increased affinity for IL-2Rα. The invention therefore includes IL-2 mutants with improved biological potency. The invention also includes methods for directed evolution of IL-2 using yeast surface display to generate mutants with increased affinity for IL-2Rα and methods of treating patients who have a condition that would benefit from T cell stimulation (e.g., a carcinoma or viral infection).

Display technologies such as phage display (Parmley and Smith, *Gene* 73:305-318, 1988) and yeast surface display (Boder and Wittrup, *Nature Biotechnol.* 15:553-557, 1997), are powerful tools that can be used for screening large libraries of protein variants for altered binding properties. Variants with enhanced receptor binding affinities have been isolated for human growth hormone (Lowman et al., *Biochem.* 30:10832-10838, 1991), interleukin-6 (Toniatti et al., *EMBO J.* 15:2726-2737, 1996) and ciliary neurotrophic growth factor (Saggio et al., *EMBO J.* 14:3045-3054, 1995), using phage display. IL-2 has been functionally displayed on phage (Buchli et al., *Arch. Biochem. Biophys.* 339:79-84, 1997), but improved mutants have not previously been engineered by phage display. To this end, IL-2 mutants with improved affinity for IL-2Rα were selected from a yeast-displayed randomly mutated library. The mutants obtained were tested for proliferation of a T cell line (KIT225; see the Examples, below).

In addition to the polypeptides, nucleic acids, and other compositions described herein for the first time, the invention includes methods to isolate IL-2 mutants with tailored binding characteristics and to characterize T cell responses to these mutants. The YT-2C2 cell-binding assay provides a convenient preliminary test to check and ensure that the mutants selected do not have greatly weakened affinities for IL-2Rβ. The methods can be used for the generation and characterization of IL-2 mutants with picomolar affinities for IL-2Rα (having increased biological potency relative to wild-type IL-2 or C125S).

Mutant IL-2 Polypeptides

The invention features mutant IL-2 polypeptides, which may be, but are not necessarily, substantially purified and which can function as an agonist of wild-type IL-2 (carrying out one or more of the biological activities of IL-2 (e.g., stimulation of cellular proliferation)). IL-2 has been characterized as a T cell growth factor that induces proliferation of antigen-activated T cells and stimulation of NK cells.

A mutant IL-2 polypeptide includes (or, in other embodiments, is limited to) an amino acid sequence that is at least 80% identical to SEQ ID NO:2 and that binds an IL-2 receptor α subunit (IL-2Rα) with an affinity that is greater than the affinity with which the polypeptide represented by SEQ ID NO:3 binds the IL-2Rα. For example, a mutant IL-2 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2, and that binds the IL-2Rα with higher affinity than a wild-type IL-2. For example, where the mutant IL-2 polypeptide is mutant only by virtue of amino acid substitutions, up to 26 amino acid residues of SEQ ID NO:2 can be changed.

The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., *Nucleic Acids Res.* 12:387, 1984), BLASTP, BLASTN, FASTA (Atschul et al., *J. Molecular Biol.* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The mutant IL-2 polypeptides can be at least 50%, at least 65%, at least 70%, at least 80%, at least 85%, at least 87%, at least 90%, at least 95%, at least 97%, at least 98%, or at least 99% identical to wild-type IL-2. The mutation can consist of a change in the number or content of amino acid residues. For example, the mutant IL-2 can have a greater or a lesser number of amino acid residues than wild-type IL-2. Alternatively, or in addition, the mutant polypeptide can contain a substitution of one or more amino acid residues that are present in the wild-type IL-2. The mutant IL-2 polypeptide can differ from wild-type IL-2 by the addition, deletion, or substitution of a single amino acid residue, for example, a substitution of the residue at position 69. Similarly, the mutant polypeptide can differ from wild-type by a substitution of two amino acid residues, for example, the residues at positions 1, 11, 46, 48, 49, 61, 64, 68, 69, 71, 74, 79, 90, 101, 103, 114, 128, and 133 of SEQ ID NO:1.

By way of illustration, a polypeptide that includes an amino acid sequence that is at least 95% identical to a reference amino acid sequence of SEQ ID NO:2 is a polypeptide that includes a sequence that is identical to the reference sequence except for the inclusion of up to five alterations of the reference amino acid of SEQ ID NO: 2. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

More specifically, a mutation (whether conservative or non-conservative, by way of addition(s) or deletion(s)) can be made at one or more of positions 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 of SEQ ID NO:1. For example, the mutation can be: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, S75P, K76E, K76R, H79R, N88D, I89V, N90H, I92T, S99P, T101A, F103S, I114V, I128T, I128A, T133A, or T133N. Additions, deletions, and substitutions of more than two residues, and substitutions at other positions are likely to produce a similarly useful (i.e., therapeutically effective) mutant IL-2 polypeptide. As noted, any of the mutants described herein (e.g., the mutant M6, M1, C1, N31610__25_ (aka WE3), N31610__18_ (aka WC9), N31610__01_ (aka 1a-1), N31618__08_ (aka 1b-8), and N31618__14_ (aka 2-4) can optionally include a substitution of the cysteine residue at position 125 (e.g., a substitution to serine) and/or a deletion of the alanine residue at position 1 of SEQ ID NO:2.

Although we favor the term "polypeptide," we may also use the terms "protein" or "peptide" to refer to any chain of amino acid residues, regardless of its length or post-translational modification (e.g., glycosylation or phosphorylation). In the event the mutant IL-2 polypeptides of the invention are "substantially pure," they can be at least 60% by weight (dry weight) the polypeptide of interest, for example, a polypeptide containing the mutant IL-2 amino acid sequence. For example, the polypeptide can be at least 75%, 80%, 85%, 90%, 95% or 99%, by weight, the polypeptide of interest. Purity can be measured by any appropriate standard method, for example, column chromatography, polyacrylamide gel electrophoresis, or HPLC analysis.

With respect to affinity, the invention includes mutant IL-2 polypeptides that bind IL-2Rα with at least about 2%, at least about 5%, at least about 10%, at least about 20%, at least about 30%, or at least about 40% higher affinity than the wild-type IL-2 polypeptide (which binds the IL-2Rα with a $K_d$ of about 28 nM). Thus in some embodiments, the mutant IL-2 polypeptides will bind the IL-2Rα with a $K_d$ of less than about 28 nM (e.g., equal to or less than about 25 nM, equal to or less than about 20 nM, equal to or less than about 10 nM, equal to or less than about 5 nM, or equal to or less than about 1 nM). Alternatively, or in addition, a mutant IL-2 polypeptide can have increased potency in a T cell proliferation assay. The ability of a mutant IL-2 polypeptide to bind IL-2Rα can be assessed by numerous assays, including the KIT225 cell binding and proliferation assays described herein.

The mutant IL-2 polypeptides can also be characterized in their ability to exhibit a decreased dissociation rate from the IL-2Rα receptor subunit, such that signaling from the receptor/ligand complex persists for a longer time period following transient exposure to the mutant IL-2 polypeptide, as compared to a wild-type IL-2 or PROLEUKIN.

As described further below, we generated a class of mutant IL-2 polypeptides with increased binding affinity for the IL-2Rα using directed evolution and yeast surface display. A number of mutants were generated using the methods described herein, including M6, M1 and C1 (other mutants include M13, N31510__15_, M12, M9, M5, N31610__12_, N31510__17_, N31610__20_, N31610__23_, N31610__25_ (WE3), N31610__13_, M16, M30, N31610__18_ (WC9), N31611_, N31610__01_ (1a-1), N31610__09_, N31610__04_, N31618__08_ (16-8), and N31610__14_ (2-4); all within the scope of the present invention). Briefly, M6 and M1 have a higher affinity for IL-2RI than C1 and C125S; C1 and C125S have comparable affinities for IL-2RI. Mutant IL-2 polypeptides are described further below.

In general, the polypeptides used in the practice of the instant invention will be synthetic, or produced by expression of a recombinant nucleic acid molecule. In the event the polypeptide is a chimera (e.g., a fusion protein containing at least a mutant IL-2 polypeptide and a heterologous polypeptide), it can be encoded by a hybrid nucleic acid molecule containing one sequence that encodes all or part of the mutant IL-2, and a second sequence that encodes all or part of the heterologous polypeptide. For example, the mutant IL-2 polypeptide may be fused to a hexa-histidine tag to facilitate purification of bacterially expressed protein, or to a hemagglutinin tag to facilitate purification of protein expressed in eukaryotic cells.

The techniques that are required to make mutant IL-2 polypeptides are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of mutant IL-2 polypeptides). As one non-limiting example, the valine residue at position 69 can be changed to, for example, alanine. Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating mutant polypeptides via expression of nucleic acid molecules that have been altered by recombinant molecular biological techniques, mutant polypeptides can be chemically synthesized. Chemically synthesized polypeptides are routinely generated by those of skill in the art.

As noted above, the mutant IL-2 polypeptides can also be prepared as fusion or chimeric polypeptides that include a mutant IL-2 polypeptide and a heterologous polypeptide (i.e., a polypeptide that is not IL-2 or a mutant thereof) (see, e.g., U.S. Pat. No. 6,451,308). The heterologous polypeptide can increase the circulating half-life of the chimeric polypeptide in vivo, and may, therefore, further enhance the properties of the mutant IL-2 polypeptides. The polypeptide that increases the circulating half-life may be a serum albumin, such as human serum albumin, or the Fc region of the IgG subclass of antibodies that lacks the IgG heavy chain variable region. The Fc region can include a mutation that inhibits complement fixation and Fc receptor binding, or it may be lytic, i.e., able to bind complement or to lyse cells via another mechanism, such as antibody-dependent complement lysis (ADCC; Ser. No. 08/355,502 filed Dec. 12, 1994).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases.

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., *The Immunologist* 2:119-124, 1994; and Brekke et al., *The Immunologist* 2:125, 1994).

In other embodiments, the chimeric polypeptide can include the mutant IL-2 polypeptide and a polypeptide that functions as an antigenic tag, such as a FLAG sequence. FLAG sequences are recognized by biotinylated, highly specific, anti-FLAG antibodies, as described herein (see also Blanar et al., *Science* 256:1014, 1992; LeClair et al., *Proc. Natl. Acad. Sci. USA* 89:8145, 1992). In some embodiments, the chimeric polypeptide further comprises a C-terminal c-myc epitope tag.

In other embodiments, the chimeric polypeptide includes the mutant IL-2 polypeptide and a heterologous polypeptide that functions to enhance expression or direct cellular localization of the mutant IL-2 polypeptide, such as the Aga2p agglutinin subunit (see, e.g., Boder and Wittrup, *Nature Biotechnol.* 15:553-7, 1997).

Chimeric polypeptides can be constructed using no more than conventional molecular biological techniques, which are well within the ability of those of ordinary skill in the art to perform.

In other embodiments, a chimeric polypeptide including a mutant IL-2 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

Nucleic Acid Molecules Encoding Mutant IL-2

The mutant IL-2 polypeptide, either alone or as a part of a chimeric polypeptide, such as those described above, can be obtained by expression of a nucleic acid molecule. Thus, nucleic acid molecules encoding polypeptides containing a mutant IL-2 are considered within the scope of the invention. Just as mutant IL-2 polypeptides can be described in terms of their identity with wild-type IL-2 polypeptides, the nucleic acid molecules encoding them will necessarily have a certain identity with those that encode wild-type IL-2. For example, the nucleic acid molecule encoding a mutant IL-2 polypeptide can be at least 50%, at least 65%, preferably at least 75%, more preferably at least 85%, and most preferably at least 95% (e.g., 99%) identical to the nucleic acid encoding wild-type IL-2 (e.g., SEQ ID NO:2).

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules of the invention can include fragments not found as such in the natural state. Thus, the invention encompasses recombinant molecules, such as those in which a nucleic acid sequence (for example, a sequence encoding a mutant IL-2) is incorporated into a vector (e.g., a plasmid or viral vector) or into the genome of a heterologous cell (or the genome of a homologous cell, at a position other than the natural chromosomal location).

As described above, the mutant IL-2 polypeptide of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-2-encoding DNA obtained from any biological cell, such as the cell of a mammal. Thus, the nucleic acids of the invention (and the polypeptides they encode) can be those of a mouse, rat, guinea pig, cow, sheep, horse, pig, rabbit, monkey, baboon, dog, or cat. Typically, the nucleic acid molecules will be those of a human.

Expression of Mutant IL-2 Gene Products

The nucleic acid molecules described above can be contained within a vector that is capable of directing their expression in, for example, a cell that has been transduced with the vector. Accordingly, in addition to mutant IL-2 polypeptides, expression vectors containing a nucleic acid molecule encoding a mutant IL-2 polypeptide and cells transfected with these vectors are among the preferred embodiments.

Vectors suitable for use in the present invention include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

Prokaryotic or eukaryotic cells that contain and express a nucleic acid molecule that encodes a mutant IL-2 polypeptide are also features of the invention. A cell of the invention is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the invention.

The precise components of the expression system are not critical. For example, a mutant IL-2 polypeptide can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (*Cloning Vectors: A Laboratory Manual*, 1985 Suppl. 1987).

The expressed polypeptides can be purified from the expression system using routine biochemical procedures, and can be used, e.g., as therapeutic agents, as described herein.

Methods of Treatment

The mutant IL-2 polypeptides, and/or nucleic acids expressing them, can be administered to a subject to treat a disorder associated with abnormal apoptosis or a differentiative process (e.g., cellular proliferative disorders or cellular differentiative disorders, such as cancer, by, for example, producing an active or passive immunity).

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. The compositions of the present invention (e.g., mutant IL-2 polypeptides and/or the nucleic acid molecules that encode them) can also be administered to a patient who has a viral infection (e.g., AIDS or an influenza)

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

Patients amenable to treatment may also have psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

Alternatively, or in addition to methods of direct administration to patients, the mutant IL-2 polypeptides can be used in ex vivo methods. For example, cells (e.g., peripheral blood lymphocytes or purified populations of lymphocytes isolated from a patient and placed or maintained in culture) can be cultured in vitro in culture medium and the contacting step can be effected by adding the IL-2 mutant to the culture medium. The culture step can include further steps in which the cells are stimulated or treated with other agents, e.g., to stimulate proliferation, or to expand a population of cells that is reactive to an antigen of interest (e.g., a cancer antigen or a viral antigen). The cells are then administered to the patient after they have been treated.

Pharmaceutical Compositions and Methods of Administration

The mutant IL-2 polypeptides and nucleic acids can be incorporated into compositions, including pharmaceutical compositions. Such compositions typically include the polypeptide or nucleic acid molecule and a pharmaceutically acceptable carrier. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

A pharmaceutical composition is formulated to be compatible with its intended route of administration. The mutant IL-2 polypeptides of the invention may be given orally, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the mutant IL-2 polypeptides, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the mutant IL-2 polypeptides or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds (mutant IL-2 polypeptides or nucleic acids) can also be prepared in the form of suppositories (e.g., with conventional suppository bases such as cocoa butter and other glycerides) or retention enemas for rectal delivery.

The compounds (mutant IL-2 polypeptides or nucleic acids) can also be administered by transfection or infection using methods known in the art, including but not limited to the methods described in McCaffrey et al. (*Nature* 418:6893, 2002), Xia et al. (*Nature Biotechnol.* 20:1006-1010, 2002), or Putnam (*Am. J. Health Syst. Pharm.* 53:151-160, 1996, erratum at *Am. J. Health Syst. Pharm.* 53:325, 1996).

In one embodiment, the mutant IL-2 polypeptides or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such mutant IL-2 polypeptides or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a mutant IL-2 polypeptides (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1st International Standard for Interleukin-2 (human)). The dosage may be similar to, but is expected to be less than, that prescribed for PROLEUKIN. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the mutant IL-2 polypeptides of the invention can include a single treatment or, can include a series of treatments. In one embodiment, the compositions are administered every 8 hours for five days, followed by a rest period of 2 to 14 days, e.g., 9 days, followed by an additional five days of administration every 8 hours.

The pharmaceutical compositions can be included in a container, pack, or dispenser together with instructions for administration.

EXAMPLES

The invention is further described in, and illustrated by, the following studies that serve as non-limiting examples.

Example 1

Construction and Screening of an IL-2 Mutant Library

We subcloned the human IL-2 gene (GenBank® accession no. NM_000586) into the pCT302 backbone at NheI and BamHI restriction sites and mutated the nucleotide sequence by site directed mutagenesis to obtain a sequence encoding a serine at position 125. We refer to the polypeptide encoded by this sequence as C125S IL-2 or, more simply as "C125S" (equivalent to Proleukin™ (aldesleukin)). The vector was named pCT-IL-2. Next, we subjected the C125S coding sequence to random mutagenesis by error-prone polymerase chain reaction (PCR). We controlled the error rate by varying cycles of PCR amplification in the presence of nucleotide analogs 8-oxodGTP and dPTP (Zaccolo and Gherardi, *J. Mol. Biol.* 285:775-783, 1999; Zaccolo et al., *J. Mol. Biol.* 255: 589-603, 1996). The PCR product we obtained was further amplified by PCR without the nucleotide analogs, and the final PCR product was transformed into yeast along with linearized pCT-IL-2. Homologous recombination in vivo in yeast between the 5' and 3' flanking 50 base pairs of the PCR product with the gapped plasmid resulted in a library of approximately $5 \times 10^6$ IL-2 variants (Raymond et al., *Biotechniques* 26:134-138, 140-141, 1999).

We expressed, purified, and biotinylated a soluble ectodomain of IL-2Rα (Wu et al., *Protein Sci.* 8:482-489, 1999) in insect cell culture and expressed it as an Aga2p protein fusion in *Saccharomyces cerevisiae* EBY100 by induction in a medium containing galactose (Boder and Wittrup, *Nat. Biotechnol.* 15:553-557, 1997). Yeast cells were labeled with mAb 9e10 or biotinylated soluble IL-2Rα (as described by Boder and Wittrup, *Methods Enzymol.* 328:430-444, 2000).

Yeast cells from the IL-2 library were labeled with biotinylated soluble IL-2Rα at 37° C., at concentrations of 0.2-0.8 nM, and saturating concentration of mAb 12CA5 (Roche Molecular Biochemicals). The cells were washed, labeled with streptavidin conjugated with R-phycoerythrin (Pharmingen) and a goat anti-mouse antibody (Sigma Chemical Co., St. Louis Mo.) conjugated with FITC. The cells were then sorted on the Cytomation Moflo™ (first two sorts) or the Beckton Dickinson FACStar™ flow cytometer. After the fourth sort, DNA from twenty individual clones was extracted using the Zymoprep™ kit (Zymo Research corporation). The DNA was amplified by transforming it into XL-1 Blue cells (Stratagene). We then sequenced the IL-2 mutants.

IL-2 mutants isolated by flow cytometry were subcloned into secretion vectors, and secreted in yeast shake flask cultures, with an N-terminal FLAG epitope tag and a C-terminal c-myc epitope tag. The mutants were purified by FLAG immunoaffinity chromatography (Sigma Chemical Co.). To quantify IL-2 concentrations, we used quantitative Western blotting with a FLAG-BAP protein standard (Sigma Chemical Co.) and a mutant M6 standard.

Example 2

KIT225 Cell Proliferation Assay

KIT225 is a human IL-2 dependent T cell line, expressing roughly 3,000-7,000 IL-2Rαβγ and 200,000-300,000 IL-2Rα (Arima et al., *J. Exp. Med.* 176:1265-1272, 1992; Hori et al., *Blood* 70:1069-1072, 1987). The KIT225 cells were cultured in RPMI 1640 supplemented with 20 pM IL-2, 10% fetal bovine serum (FBS), 200 mM L-glutamine, 50 units/mL penicillin and 50 μg/mL gentamycin.

KIT225 cells were cultured in medium without IL-2 for six days. The cell culture medium was changed after three days. On the sixth day, the cells were transferred into medium containing C125S IL-2 or an IL-2 mutant at varying concentrations. Aliquots of the cell culture were taken at different times, and we determined the viable cell density using the Cell-titer Glo™ (Promega) assay.

Example 3

Binding of IL-2 Mutants to KIT225 & YT2C2

We incubated KIT225 cells ($10^6$ cells in 100 μL) with soluble C125S IL-2 or a mutant IL-2 at 37° C., pH 7.4, for 30 minutes. Cells were washed with ice-cold PBS, pH 7.4, containing 0.1% bovine serum albumin (BSA) and labeled with a biotinylated antibody against the FLAG epitope followed by streptavidin-phycoerythrin on ice. We washed the cells again and determined mean single cell fluorescence using an EPICS-XL flow cytometer.

YT-2C2 is a human NK cell line that expresses approximately 20,000 IL-2Rβγ (Teshigawara et al., *J. Exp. Med.* 165:223-238, 1987). We cultured YT-2C2 cells in the same medium we used to culture KIT225 cells, without IL-2 or with IL-2 or IL-2 mutants, on ice, for 30 minutes at pH 7.4 ($10^6$ cells in 100 μL). The cells were washed with ice-cold PBS (pH 7.4, 0.1% BSA) and labeled with a biotinylated antibody against the FLAG epitope followed by exposure to streptavidin-phycoerythrin on ice. The cells were washed again and mean single cell fluorescence was determined using an EPICS-XL flow cytometer. The equilibrium dissociation constants were determined using a global fit. We calculated 66% confidence intervals as described by Lakowicz (*Principles of Fluorescence Spectorscopy*, 1999).

Example 4

Functional Expression of IL-2 on the Surface of Yeast

Although IL-2 has been displayed on bacteriophage previously (Buchli et al., *Arch. Biochem. Biophys.* 339:79-84, 1997), the prior system was not amenable to directed evolution and therefore not suitable for obtaining IL-2 mutants with improved binding for subunits of the IL-2R. We expressed IL-2 on the surface of yeast cells, assuming that expression in a eukaryotic system would produce a higher fraction of correctly folded protein. More specifically, IL-2 was expressed as a fusion with the Aga2p agglutinin subunit as described by Boder and Wittrup (*Nat. Biotechnol.* 15:553-557, 1997). We measured the expression of the Aga2p-IL-2 fusion on the surface of yeast by immunofluorescent labeling of the C-terminal c-myc epitope tag (FIG. 1A). IL-2 displayed on the surface of yeast binds specifically to the soluble ectodomain of IL-2Rα (FIG. 1B), while negative control yeast displaying an irrelevant scFv do not (compare FIG. 1C and FIG. 1D).

Example 5

Screening of IL-2 Library for Clones with Improved Binding to IL-2Rα

The yeast-displayed library of IL-2 mutants described above was screened through four rounds of sorting by flow cytometry, with regrowth and reinduction of surface expression between each sort, to isolate clones with improved binding to soluble IL-2Rα. The ensemble of clones after four rounds of sorting shows improved binding relative to C125S at 0.4 nM soluble IL-2Rα, normalized to the number of IL-2 fusions on the yeast surface (FIGS. 2A-2B).

Twenty mutants were sequenced (Table I), and seven distinct sequences were obtained from these twenty clones. The most frequently occurring mutations (V69A and Q74P) cluster in a region predicted to be at the IL-2/IL-2Rα interface, by a homology model of IL-2 binding to its receptor subunits (FIG. 3). The mutant M6 also has a mutation I128T, which is close to the predicted IL-2/IL-2β and IL-2/IL-2Rγ interface (Bamborough et al., *Structure* 2:839-851, 1994; Berman et al., *Nucleic Acids Res.* 28:235-242, 2000).

TABLE I

Mutations in IL-2 Clones with Greater Affinity for IL-2Rα Compared to C125S.

| | | Mutants | | | | | | |
|---|---|---|---|---|---|---|---|---|
| | | M16 | M13 | M12 | M9 | M5 | M30 | M6 |
| | | Isolates | | | | | | |
| Position | WT aa | 1 | 3 | 7 | 4 | 1 | 1 | 3 |
| 1 | A | T | | | | | | |
| 11 | Q | | | | | | R | |
| 46 | M | L | | | | | | |
| 48 | K | | | | | | E | |
| 49 | K | R | | | | | | |
| 61 | E | D | | | | | | |
| 64 | K | | | R | | | | |
| 68 | E | | | | | | D | |
| 69 | V | A | A | A | A | A | | A |
| 71 | N | | | | | | T | |
| 74 | Q | | | P | P | P | | P |
| 79 | H | R | | | | | | |
| 90 | N | | | | | | H | |
| 101 | T | | | | A | A | | |
| 103 | F | | | | | | S | |
| 114 | I | | | | | | V | |
| 128 | I | | | | | | | T |
| 133 | T | | | | | N | | |

Example 6

Binding of IL-2 Mutants to KIT225 Cells Expressing an Excess of IL-2Rα

The IL-2 mutants we isolated by yeast surface display were tested in soluble form for tighter binding to IL-2Rα on the surface of KIT225 cells. Three different mutants were tested: M6 (V69A, Q74P, I128T), M1 (V69A, Q74P), and C1 (I128T). M1 represents the most frequently occurring mutations, C1 represents the mutation predicted to be close to the IL-2/IL-2β and IL-2/IL-2Rγ interface, and M6 is one of the clones isolated after four rounds of sorting using flow cytometry.

FIG. 4 shows representative data for binding of M6, M1, C1, and C125S IL-2 to KIT225 cells at 37° C. M6 and M1 bind KIT225 cells similarly, while C1 binds in a manner reminiscent of C125S. Since the KIT225 cells express an excess of IL-2Rα, relative to IL-2Rβ and IL-2Rγ, the binding data obtained corresponds to IL-2Rα a binding. Thus, M6 and M1 have a higher binding affinity for IL-2Rα on the surface of KIT225 cells, as compared to C1 and C125S IL-2. The equilibrium dissociation constant ($K_d$) for C1 and C125S can only be estimated from this data, due to the rapid dissociation of IL-2Rα-bound IL-2 (Liparoto et al., *Biochemistry* 41:2543-2551, 2002). On the basis of data shown in FIG. 5, the $K_d$ for M6 and M1 can be estimated as approximately 1 nM. This represents roughly a thirty-fold minimum improvement in binding affinity, relative to a wild-type $K_d$ value of 28 nM (Liparoto et al., *Biochemistry* 41:2543-2551, 2002).

Example 7

Binding of IL-2 Mutants to YT-2C2 Cells Expressing IL-2Rβ and IL-2Rγ

We examined the binding of M1, M6, and C1 to YT-2C2 cells expressing IL-210 and IL-2Rγ (see FIGS. 5A-5D). A global fit was used to estimate the equilibrium dissociation constants ($K_d$; see Table II). The $K_d$ values are consistent with reported affinities for the binding of IL-2 to IL-2Rβ (Liparoto et al., *Biochemistry* 41:2543-2551, 2002). M1 had a significantly lower binding affinity for IL-2Rβ than C125S, M6, or C1. This is interesting in light of M1's mutation sites, predicted to be on the opposite side from IL-2's contacts with IL-2Rβ.

TABLE II

Binding affinities of IL-2 mutants for IL-2Rβ on YT-2C2 cells

|  | $K_d$ (nM) | 66% confidence intervals |
|---|---|---|
| WT (C125S) | 94 | 70-135 |
| C1 | 132 | 110-161 |
| M6 | 210 | 149-331 |
| M1 | 480 | 388-630 |

Example 8

Proliferation of IL-2 Dependent KIT225 Cells in Response to IL-2 Mutants

We studied the proliferation of a T cell line (KIT225) in response to our IL-2 mutants to evaluate the effect of the increased affinity IL-2Rα on biological potency. At low concentrations (0.5 pM) and long times, C1 and M6 caused approximately 50-60% greater proliferation of IL-2 dependent KIT225 cells in cell culture, as compared to C125S IL-2 and M1. The proliferation of KIT225 cells in culture with the different mutants, at different initial concentrations, is shown in FIGS. 6A-6F. We noted that both M6 and C1 had slightly improved biological potency while M1, with an affinity comparable to that of M6 for IL-2Rα, did not (at least under these conditions). A thirty-fold increase in the affinity of IL-2 for IL-2Rα did not have an appreciable effect on biological potency for mutant M1, suggesting that such an increase in affinity for IL-2Rα alone is not responsible for the increased potency of M6.

Example 9

Viability of KIT225 Cells in the Presence of IL-2 Mutants

To simulate the rapid clearance of IL-2 from the body, an in vitro assay with KIT225 cells was designed. KIT225 is a human IL-2 dependent T cell line, expressing roughly 3,000-7,000 IL-2Rαβγ and 200,000-300,000 IL-2Rαsgs (Arima et al., *J. Exp. Med.* 176:1265-72, 1992; Hori et al., *Blood* 70:1069-72, 1987). KIT225 cells, at 100,000-150,000 cells/mL, grown in media without IL-2 for two days, were exposed to a 2 nM concentration IL-2 or IL-2 mutant dose for 30 minutes at 37° C. The cells were then washed and transferred to medium without IL-2. Cell culture aliquots were taken at different times and the viable cell density was determined using the Cell-titer Glo™ (Promega) assay.

Figure 7A:
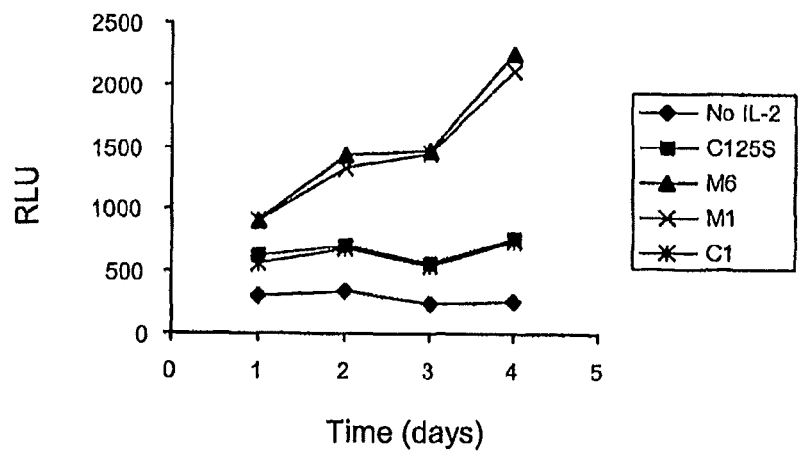
FIGS. 7A-7B are line graphs illustrating the proliferation of IL-2 dependent KIT225 cells in response to C125S and IL-2 mutants. Viable cell density was plotted over time in terms of luminescence units (FIG. 7A). We also measured the number of cells per ml at varying concentrations of C125S and IL-2 mutants.

FIG. 7A shows the viable cell density (plotted as luminescence units) as a function of time, for the different mutants. Cells exposed to M6 and M1 have a significantly greater viable cell density, sustained over a long period of time. We believe the mechanism through which these mutants act is by increased persistence on the cells through a decreased dissociation rate from the IL-2:IL-2Rα complex and hence a higher affinity for IL-2Rα.

Figure 7B:
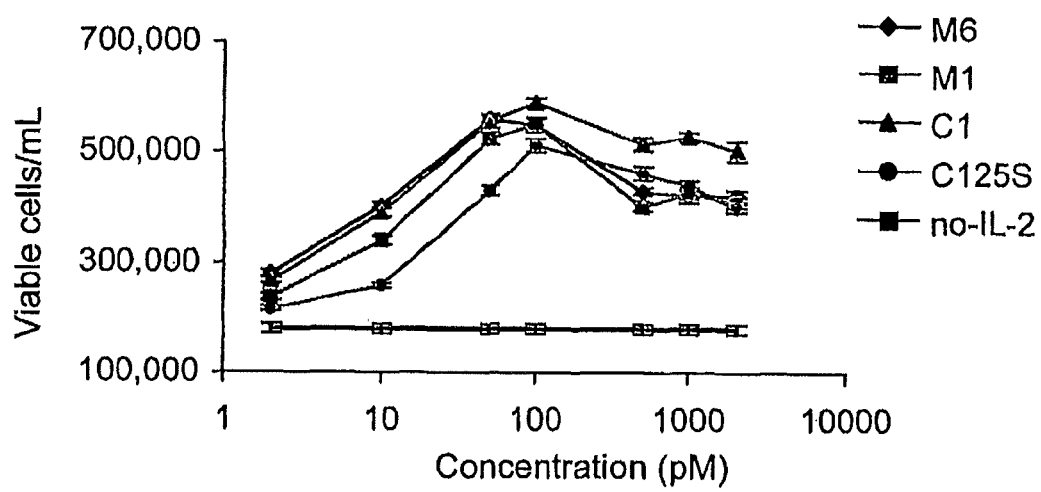

Viable cell density was also measured in cells exposed to different concentrations of C125S or IL-2 the mutants M6, M1, and C1. M6, M1, and C1 all have improved potency relative to C125S (see FIG. 7B).

Example 10

Steady State Vs. Pulse Assays

In most of the assays described above, a culture of T cells is incubated with IL-2; the IL-2 is added at a certain concentration at the beginning of the experiment, and the culture is not externally manipulated for the duration of the experiment. In such steady-state experiments, IL-2 may be degraded following internalization of the receptor/ligand complexes, but otherwise the extracellular IL-2 concentration does not change rapidly with time. This is in contrast to the rapid pharmacokinetic clearance of IL-2 in vivo, where the circulating half-life is approximately 20 minutes. Consequently, the standard steady-state assay allows sustained exposures to very low levels of IL-2 that are not realized in the clinical setting, where instead cells are exposed to a high concentration of IL-2 for a short time. To mimic such a situation experimentally, we exposed T cells to a high concentration of IL-2 for a 30-minute pulse, washed the cells, then followed their growth over several days. This experiment was repeated three times, and a representative set of data is described below. In essence, M1 and M6 stimulate sustained T cell growth under transient pulse conditions, while IL-2 stimulates only minimal growth. This capability of M1 and M6 is in contrast to their behavior in the steady state assays described above, wherein there was only a marginal activity improvement for C1 and M6, while M1 did not show improved activity. Thus, in order to identify IL-2 mutants with improved clinical properties, the pulse-type transient assay is important, if not essential.

To simulate the rapid clearance of IL-2 from the body, we designed an in vitro assay with KIT225 cells (the human IL-2 dependent T cell line described above; see also Arima et al., *J. Exp. Med.* 176:1265-1272, 1992; Hori et al., *Blood* 70:1069-1072, 1987). KIT225 cells, at 100,000-150,000 cells/mL, grown in medium without IL-2 for two days, were exposed to a 2 nM concentration of IL-2 (C125S) or an IL-2 mutant (at the same dose) for 30 minutes at 37° C. The cells were then washed and transferred to medium without an IL-2 component. Cell culture aliquots were taken at different times and the viable cell density was determined using the Cell-titer Glo™ (Promega) assay.

The mutants considered in this assay were M6, M1 and C1, in addition to C125S. Briefly, M6 and M1 have a higher affinity for IL-2Rα than C1 and C125S, which have comparable affinities for IL-2Rα.

Figure 8:
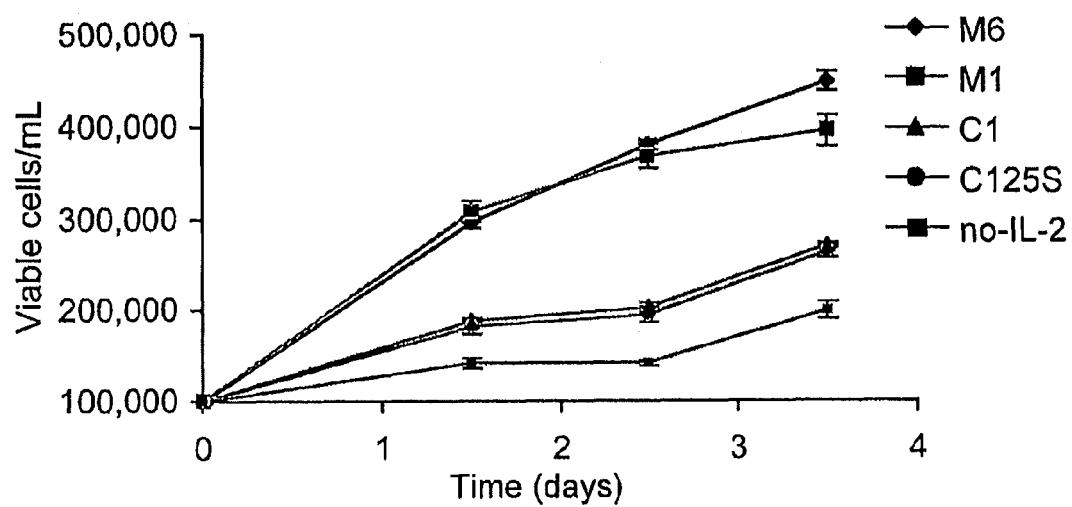
FIG. 8 is a line graph illustrating viable cell density (cells/ml) without treatment (i.e., in the absence of IL-2) and following treatment with wild type IL-2 and mutants thereof (M6, M1, and C1) over 3.5 days.

The assay described above was repeated with a pulse concentration of 1000 pM, and we determined the viable cell density over a three and one-half day time period. We plotted viable cell density (as luminescence units) over time for the different mutants (see FIG. 8).

Figure 9:
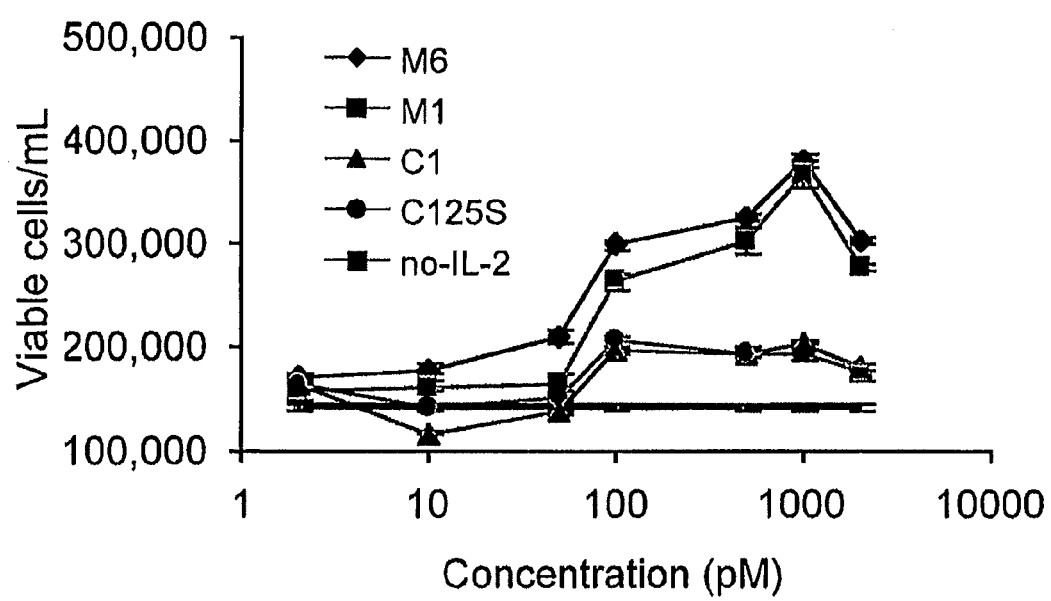
FIG. 9 is a line graph illustrating viable cell density (cells/ml) without treatment (i.e., in the absence of IL-2) and following treatment with various concentrations of C125S and the mutants M6, M1, and C1. Cell density was measured 60 hours after treatment.

We also repeated the pulse assay with varying concentrations of IL-2 and IL-2 mutants and determined viable cell density at 60 hours. Higher cell densities were observed when the cells were pulsed with M1 and M6 than when pulsed with C1, C125S, or no IL-2 (see FIG. 9).

These data show that cells exposed to M6 and M1 have a significantly greater viable cell density, sustained over a long period of time. We believe the mechanism by which these mutants act is by increased persistence on the cells by virtue of a decreased dissociation rate (and hence have a higher affinity for IL-2Rα; the invention is not limited to mutant IL-2 polypeptides that act by any particular or given mechanism). This strongly indicates that the mutants of the genus represented by M6 and M1 (i.e., mutants with increased binding affinity for IL-2Rα and decreased dissociation rate from the IL-2-IL-2Rα complex), will be better than C125S from a therapeutic perspective. An increase in affinity and a decrease in dissociation rate should be helpful by allowing a decrease in the concentration of the therapeutic pulse administered. This should, in turn, reduce any toxicity associated with IL-2-based therapeutics. At lower dosages, stimulation of NK cells through the IL-2Rβγ should be negligible. The minimum concentration of the IL-2 pulse (we refer to IL-2 here broadly; we mean to encompass IL-2 mutants and therapeutics based on these mutants) is governed by the kinetics of binding of IL-2 with IL-2Rα. At very low concentrations (~10 pM) clearance from the body would be faster than approach to saturation of the IL-2Rα sites on activated T cells. Low dosages would also potentially circumvent any immunogenicity issues with the IL-2 mutants. We believe the decrease in dissociation rate is also responsible for the sustained signaling leading to the increased cell proliferation we observed.

Example 11

Identification of New Clones with Enhanced IL-2Rα Binding Affinity

To identify further sequences with enhanced affinity for IL-2Rα, human IL-2 was mutagenized by error prone PCR and displayed on yeast. The mutants M1 and M6 were mixed with mutated IL-2 via DNA shuffling, displayed on yeast, and screened for slower dissociation from IL-2Rα by competition with soluble unlabeled wild type IL-2. We identified a pool of clones having a dissociation rate from IL-2Rα that is slower than that for M1 or M6. A sample of sequences of the mutants isolated in the first round of selection and in this second round of selection are shown in FIGS. 11A and 11B.

Example 12

Comparison of Cell-Surface Persistence of IL-2, IL-2 Mutants, and IL-15

Both IL-2 and IL-15 bind the IL-2/15Rβγ heterodimeric receptor with similar affinity ($K_d$~1 nM) and can signal through IL-2/15Rβγ in the absence of their private alpha receptor subunits. However, the two interleukins differ in their binding to the private alpha receptor subunits. IL-15 has a high binding affinity for IL-15Rα ($K_d$~10 pM), while IL-2 binds with a lower affinity to IL-2Rα ($K_d$~10 nM). This leads to prolonged persistence of IL-15, but not IL-2, on the surface of T cells in in vitro assays where cytokine is withdrawn from the medium (Dubois et al., *Immunity* 17:537-547, 2002). We hypothesized that the contrasting behavior of IL-2 and IL-15 is due to the differing persistence on the cell surface, which arises from the different affinities for their private alpha receptor subunits. IL-2 mutants with IL-2Rα affinities comparable to IL-15 would be functionally equivalent to IL-15.

Figure 12:
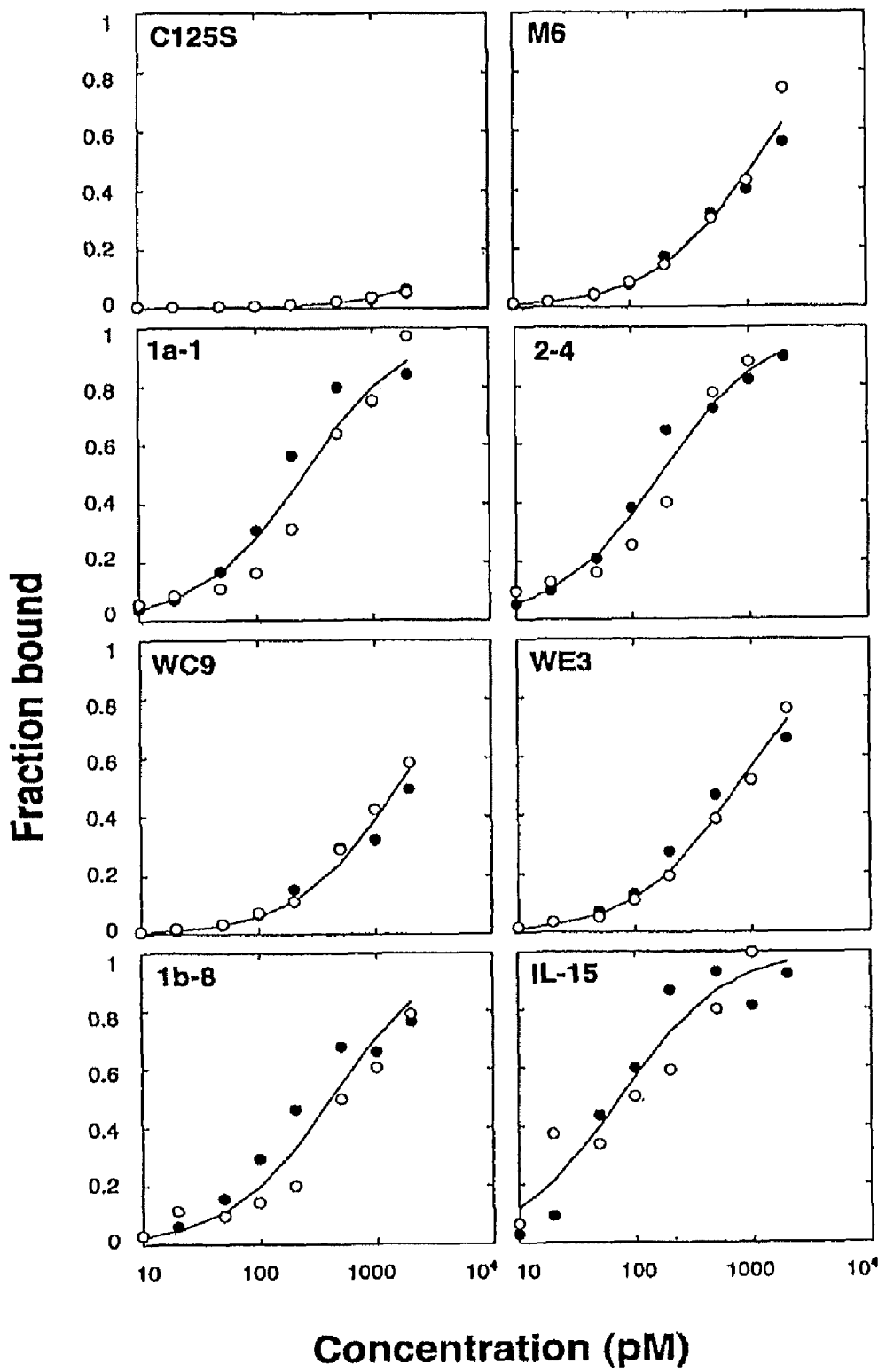
FIG. 12 is a set of graphs depicting results of experiments to determine the affinity of C125S, the IL-2 mutants M6, 1a-1, 2-4, WC9, WE3, and 1b-8), and IL-15 for IL-2Rα. Cell surface bound protein was measured using flow cytometry (Fraction bound vs. concentration (pM)).

To test our hypothesis, we compared IL-2 mutants with a range of affinities for IL-2Rα that approach the affinity of IL-15 for IL-15Rα (Table III) with IL-15 in the T cell line F15R-Kit, which expresses both IL-2Rα and IL-15Rα subunits. F15R-Kit cells expressing IL-2Rα and IL-15Rα were labeled with C125S, IL-2 mutants or IL-15 for 30 minutes at 37° C. (pH 7.4). Cell surface bound protein was measured using flow cytometry. Data from two different experiments (FIG. 12) were used to estimate $K_d$ values.

TABLE III

| IL-2 mutants with increased IL-2Ra binding affinity. | | | |
|---|---|---|---|
| Protein | Mutations | $K_d$ (pM) | 66% Confidence Intervals |
| C125S (WT) | — | 30030 | ND |
| WC9 | S4P, T10A, Q11R, V69A, Q74P, N88D, T133A | 1585 | 950-2700 |
| M6 | V69A, Q74P, I128T | 1215 | 740-2000 |
| WE3 | N30S, V69A, Q74P, I128T | 778 | 400-1270 |
| 1b-8 | K8R, Q13R, N26D, N30T, K35R, T37R, V69A, Q74P, I92T | 409 | 230-690 |
| 1a-1 | N30S, E68D, V69A, N71A, Q74P, S75P, K76R, N90H | 254 | 150-420 |
| 2-4 | N29S, Y31H, K35R, T37A, K48E, V69A, N71R, Q74P, N88D, I89V | 180 | 110-300 |
| IL-15 | — | 76 | 52-110 |

Pulse bioassays (described in Example 10, above), where cells are exposed to cytokine only for a short period of time, were used to mimic bolus pharmacokinetics. Our objective was to quantitatively analyze the relationships between affinity, persistence, and biological response for IL-2 and IL-15.

In pulse assays, IL-15 persists on the cell surface for over two days, while wild-type IL-2 has negligible persistence on the cell surface (FIGS. 13A-13D). This result is consistent with data obtained in assays where cytokine is withdrawn from the medium. IL-2 mutants with increased IL-2Rα affinity however, have increased persistence on the cell surface relative to wild-type IL-2 (FIGS. 13B, 13C, 13D). We believe this is because IL-2Rα acts as a capture reagent for high IL-2Rα affinity IL-2 mutants. We did not observe any perceptible binding of the IL-2 mutants to IL-15Rα.

Figure 14:
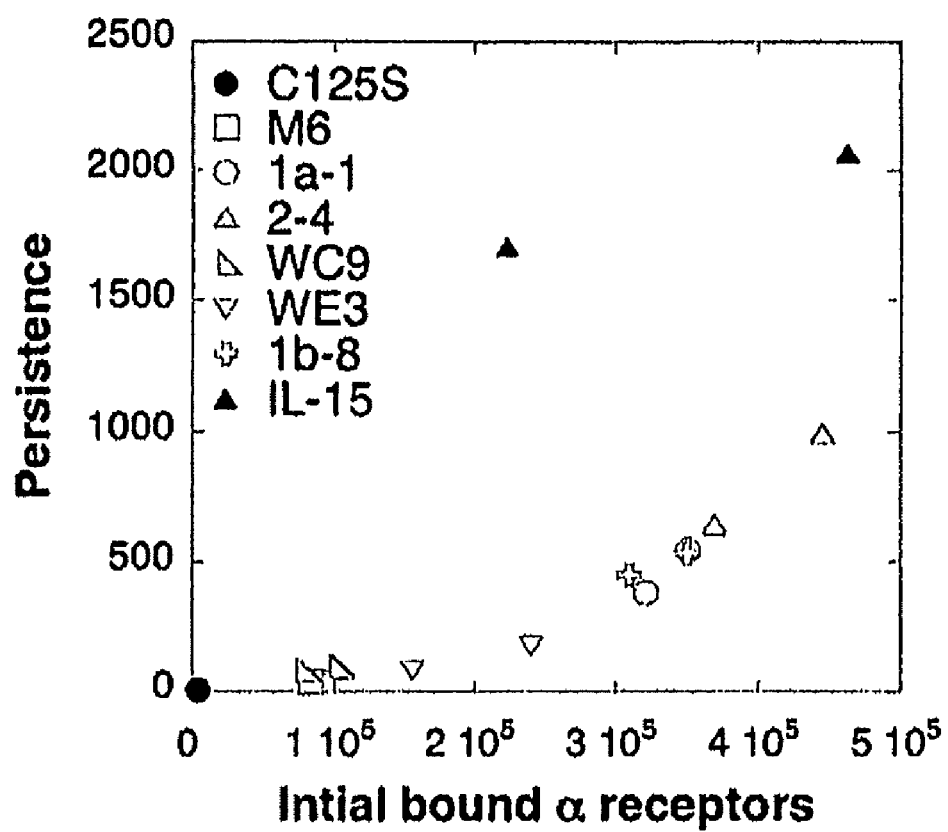
FIG. 14 is a graph depicting the persistence of C125S, IL-15, and various IL-2 mutants vs. the number of initial bound a receptors.

The area under the curve of a plot of cell-surface-bound ligand versus time serves as a quantitative definition of the persistence of the ligand on the cell surface. Increased initial private alpha receptor occupancy after cytokine withdrawal leads to increased cell surface persistence of cytokine (FIG. 14). The initial receptor occupancy is a function of binding affinity. Thus, increased affinity for the private alpha receptor subunit correlates strongly with increased cell surface persistence.

The increased persistence of high IL-2Rα affinity IL-2 mutants is conceivably due to decreased dissociation of the mutants from cell surface IL-2Rα and increased recycling of the IL-2Rα subunits. Increased affinity for the private alpha subunit leads to decreased dissociation of cell surface receptor-bound ligand. Binding of both IL-15 and IL-2 leads to internalization of the receptor-ligand complex. However, the high affinity of IL-15 for IL-15Rα causes recycling of IL-15 bound to IL-15Rα to the cell surface (Dubois et al., *Immunity* 17:537-47, 2002). Analogously, high IL-2Rα affinity IL-2 mutants have improved binding to IL-2Rα, relative to wild-type IL-2, even at endosomal pH and conceivably recycle to a greater extent than wild-type IL-2 (Fallon et al., *J. Biol. Chem.* 275:6790-7, 2000). Recycling of internalized ligand leads to higher levels of cell surface-associated ligand.

Figure 15:
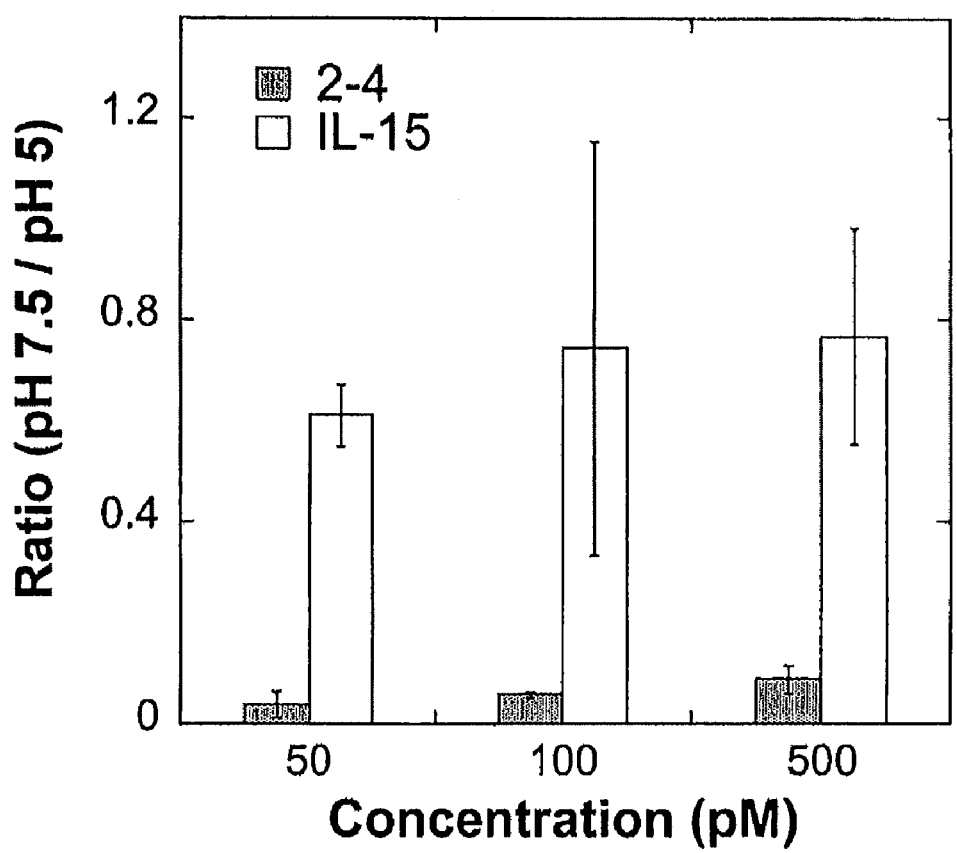
FIG. 15 is a bar graph depicting the ratio of binding of mutant 2-4 (shaded bars) and IL-15 (open bars) to receptor at pH 7.5 vs. pH 5.0 at three concentrations (50 pM, 100 pM, and 500 pM).

For a given initial receptor occupancy, IL-15 has a much greater persistence than the IL-2 mutants (FIG. 14). This can be explained by the significantly lesser sensitivity of the IL-15/IL-15Rα binding interaction to lowered pH relative to the binding of IL-2 mutants to IL-2Rα. Binding of both 2-4 (the highest CD25 affinity IL-2 mutant), and IL-15 to their respective alpha receptor subunits is decreased at pH 5 (relative to pH 7.5). However, the degree of decrease in binding at pH 5 (relative to pH 7.5) is significantly greater for 2-4 than IL-15 (FIG. 15). The significantly lesser sensitivity of IL-15 binding to IL-15Rα at endosomal pH implies that IL-15 recycles to a much greater extent than the IL-2 mutants, leading to increased persistence for a given initial receptor occupancy.

Figure 16:
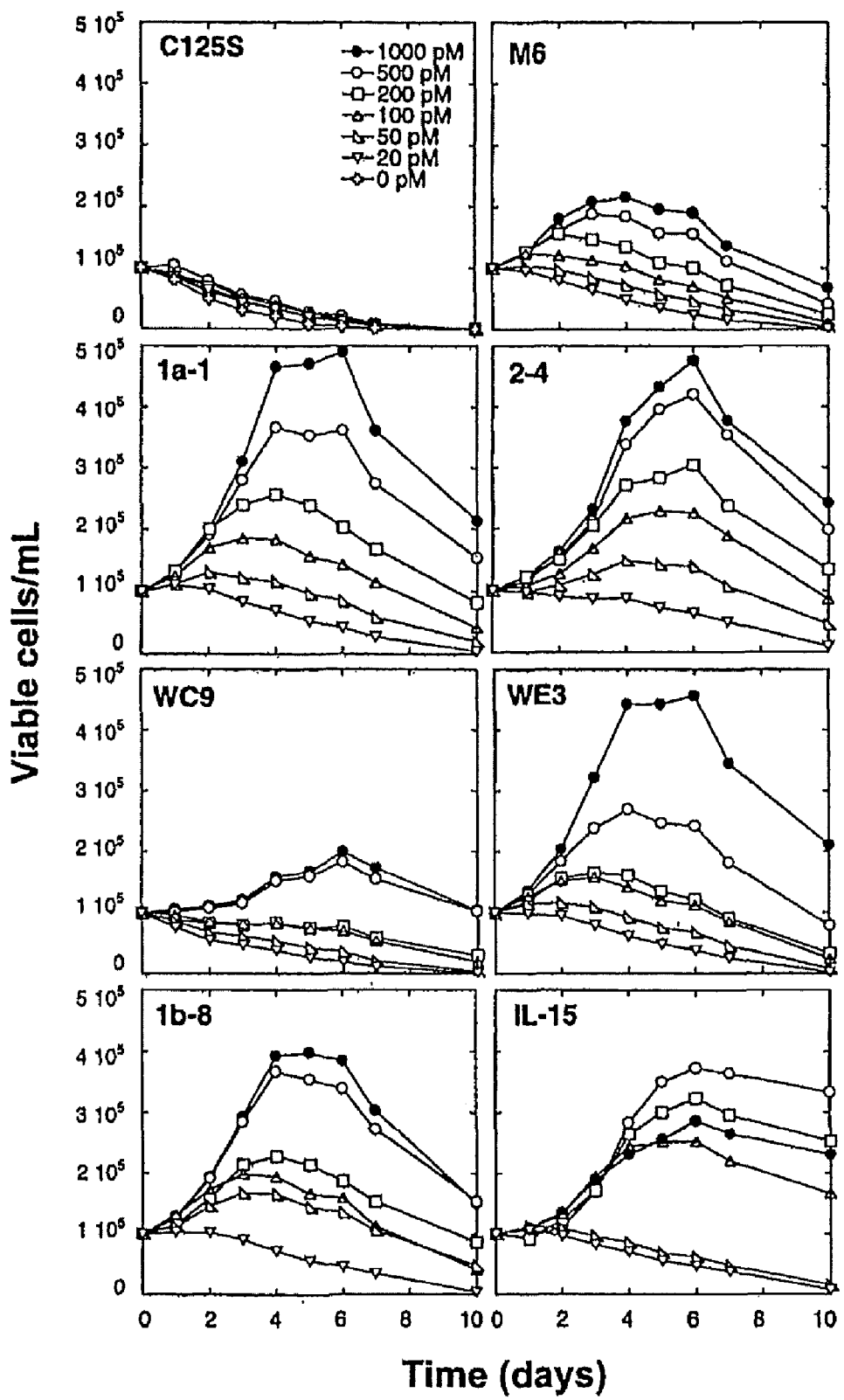
FIG. 16 is a series of graphs depicting viable cell density (cells/mL) vs. time (days) for cells treated with various concentrations of C125S, IL-2 mutants (M6, 1a-1, 2-4, WC9, WE3, and 1b-8) and IL-15.
Figure 17A:
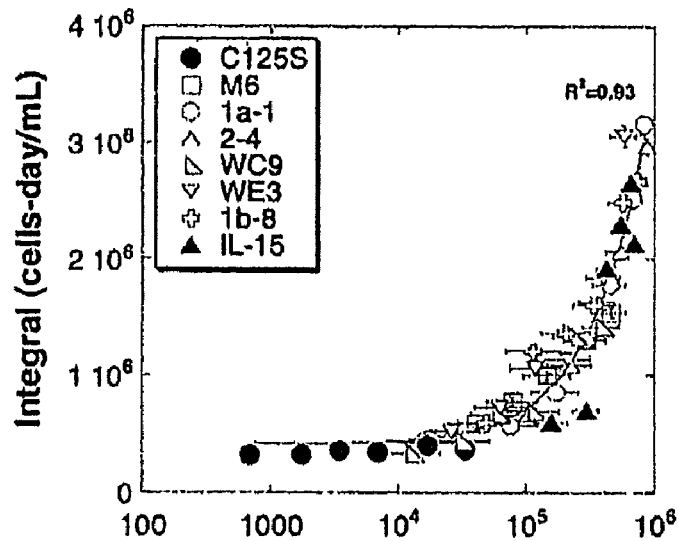
FIGS. 17A-17B are graphs depicting the growth response of 15R-Kit cells as quantified by the integral of viable cell density over a ten-day period. The maximum cell density linearly correlates with initial receptor occupancy for C125S, IL-2 mutants (M6, 1a-1, 2-4, WC9, WE3, and 1b-8) and IL-15. The total numbers of IL-2Rα and IL-15Rα were determined experimentally. The initial receptor occupancy was estimated using $K_d$ values and the total receptor number. X-error bars represent error in estimating initial receptor occupancy due to error in $K_d$ value estimates. Y-error bars represent standard deviation of triplicate measurements.
Figure 17B:
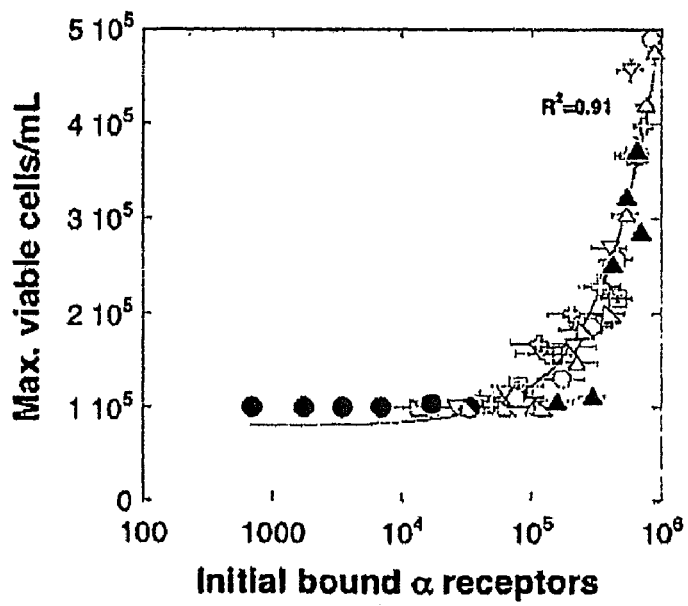
Figure 18:
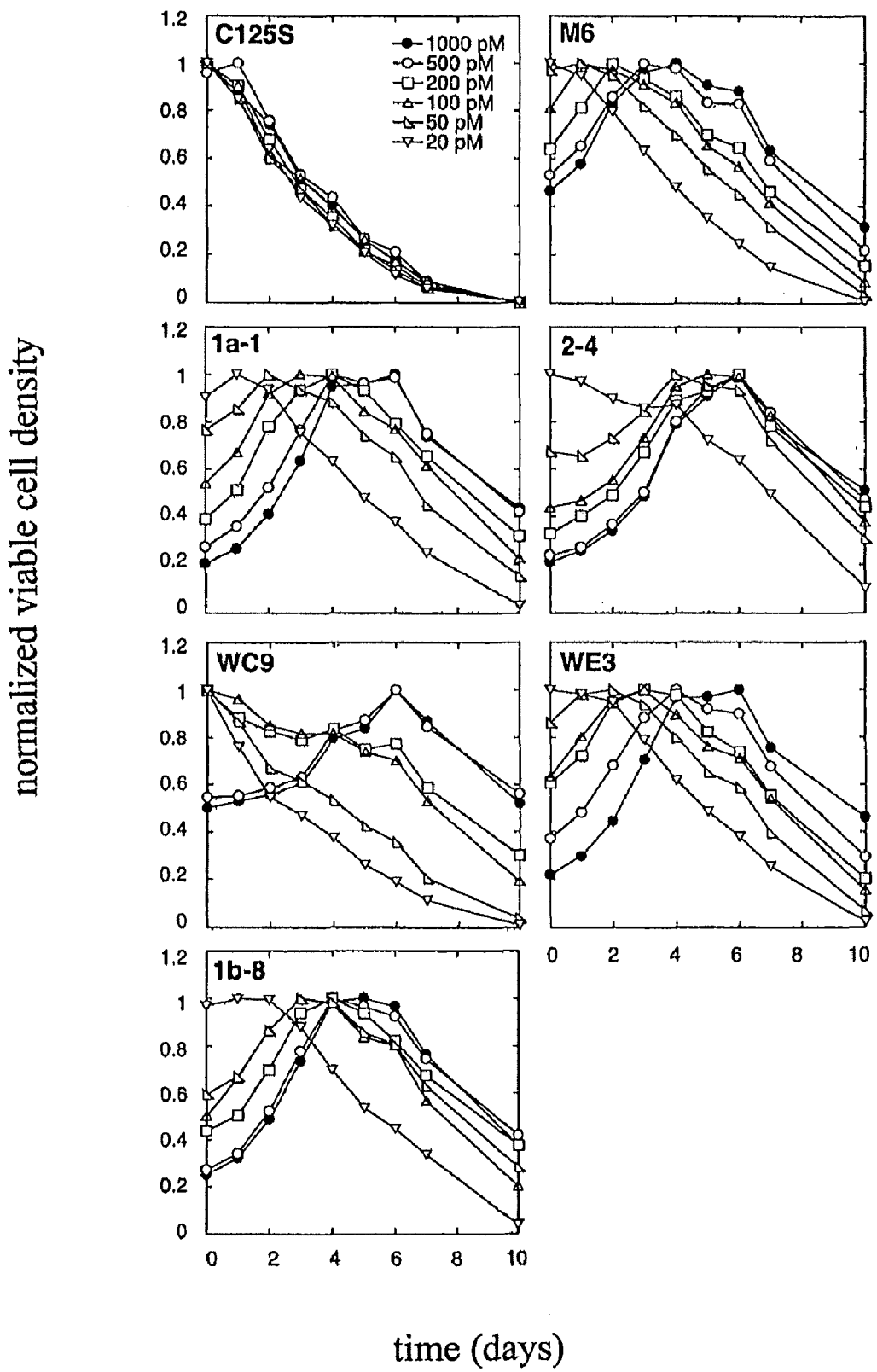
FIG. 18 is a set of graphs depicting normalized viable cell density vs. time (days) for C125S and various IL-2 mutants (M6, 1a-1, 2-4, WC9, WE3, and 1b-8).
Figure 19:
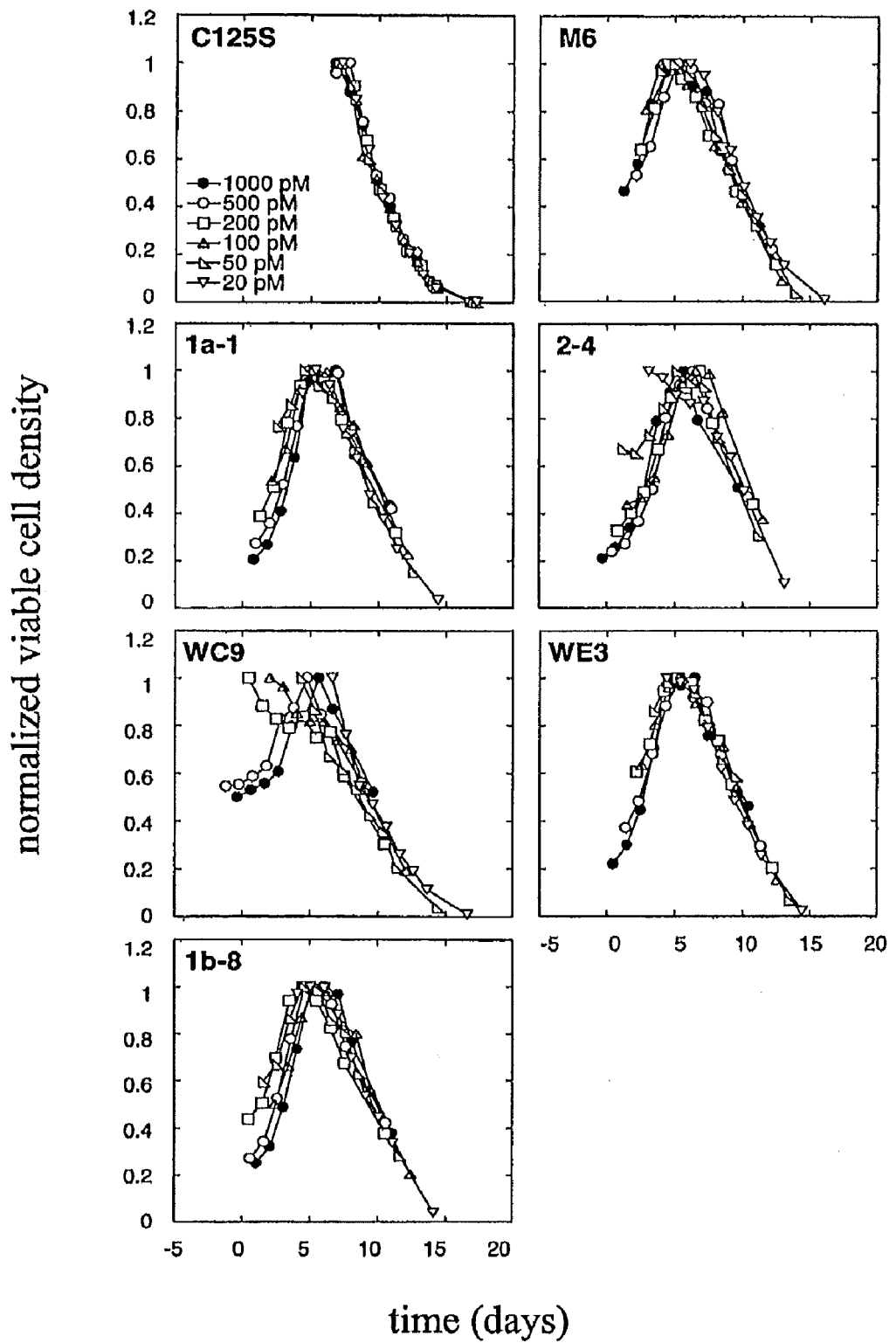
FIG. 19 is a set of graphs depicting normalized viable cell density vs. time (days) for C125S and IL-2 mutants (M6, 1a-1, 2-4, WC9, WE3, and 1b-8). In this figure, the growth curves from FIG. 18 have been shifted in the time axis such that viable cell density extrapolates to zero after at least 14 days.
Figure 20:
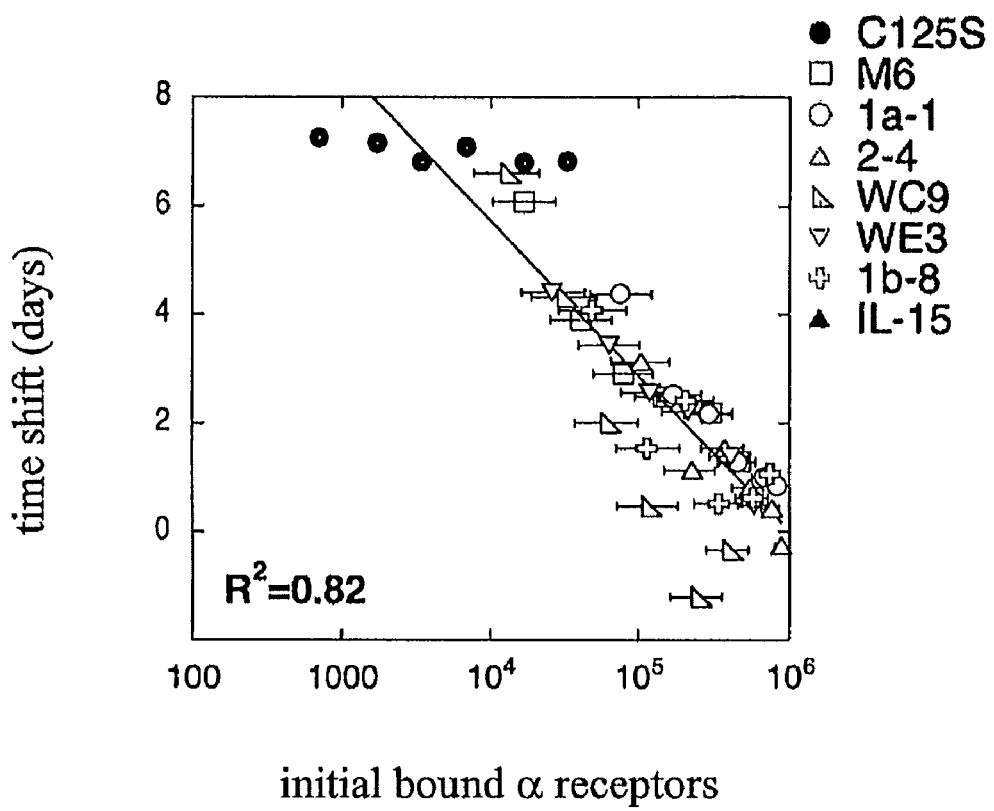
FIG. 20 is a graph depicting the number of initial bound a receptors vs. time shift (days) of C125S and IL-2 mutants.
Figure 21A:
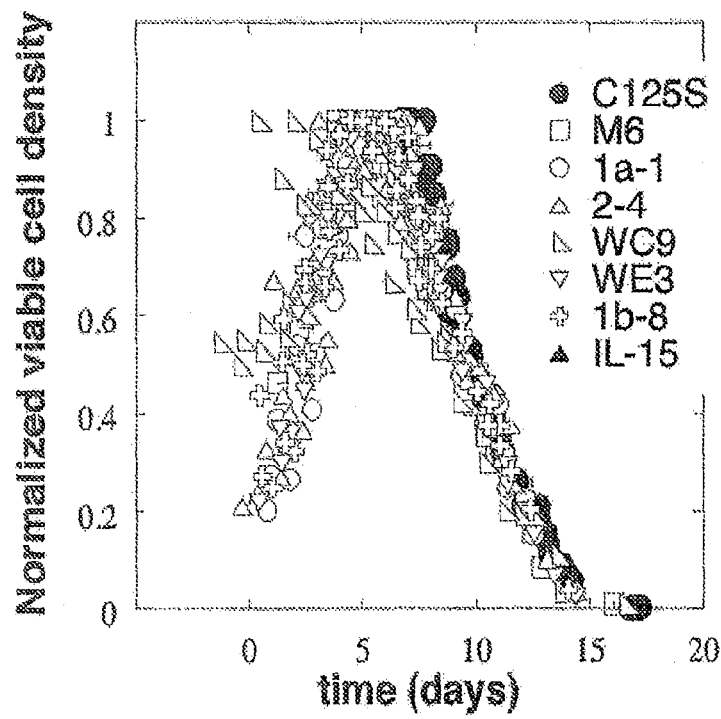
FIGS. 21A-21B are graphs depicting the growth kinetics of C125S and IL-2 mutants (FIG. 21A) and IL-15 (FIG. 21B). Normalized viable cell density is plotted vs. time (days) in each figure.
Figure 21B:
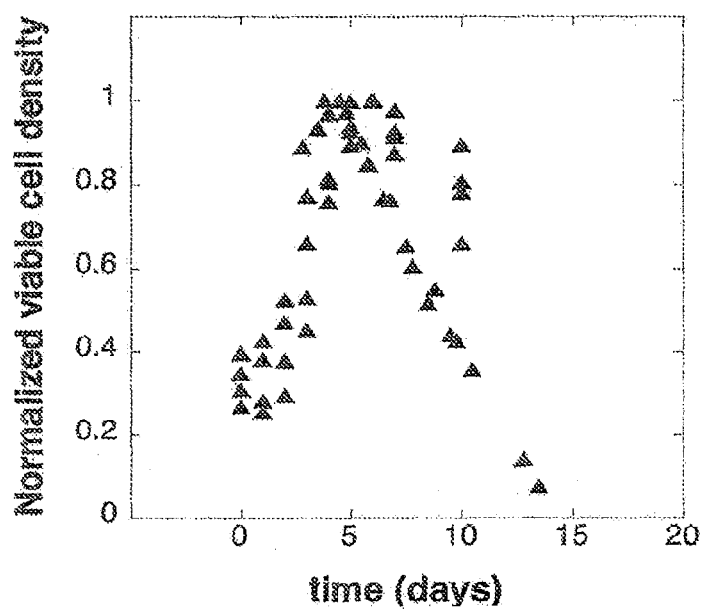

Cell surface bound IL-2 and IL-15 mediate growth signaling through the beta and gamma receptor subunits on cells. Also, both IL-2 and IL-15 on one cell can mediate signaling through the beta and gamma subunits on adjacent cells (Eicher and Waldmann, *J. Immunol.* 161:5430-5437, 1998). We have shown that an IL-2 mutant with increased IL-2Rα binding affinity persists longer in cell surface IL-2Rα reservoirs and mediates increased T cell growth. Here, we quantitatively compared the T cell growth response mediated by IL-15 and high IL-2Rα affinity IL-2 mutants in a pulse assay to understand the relationship between cell surface persistence and bioactivity. Consistent with observed in vivo behavior, IL-15 promotes the growth of T cells in a pulse assay, unlike C125S (FIG. 16). This is because an insignificant amount of wild-type IL-2 is associated with IL-2Rα on the cell-surface whereas IL-15 persists in IL-15Rα ligand reservoirs on the cell surface for a prolonged period of time. With increased IL-2Rα binding affinity, the amount of IL-2 associated with IL-2Rα increases. This leads to prolonged cell surface persistence of IL-2 mutants and hence increased growth of T cells (FIG. 16). The IL-2 mutants have substantially increased potency for T cell proliferation, relative to wild-type IL-2. Picomolar concentrations of IL-2 mutants sustain the T cell response at levels that cannot be attained using C125S, even at nanomolar concentration.

Example 13

Cell Growth Responses to IL-2 Mutants

We sought to establish a quantitative relationship between the T cell growth response and initial receptor occupancy after cytokine withdrawal and hence cytokine persistence on the cell surface. Existence of a universal relationship between cell surface persistence and T cell growth response for the IL-2 mutants and IL-15 would suggest quantitative functional equivalence of growth signaling mediated by the IL-2 mutants and IL-15. Two aspects of the T cell growth response are critical: the number of viable cells in culture and the time for which cell viability is maintained. We used the maximum viable cell density attained and the integral of viable cell number over a ten-day period as metrics to quantify the growth response to IL-2 mutants and IL-15. As explained earlier, initial receptor occupancy correlates strongly with cell surface persistence and was used as a metric for cell surface persistence. The initial number of interleukin molecules (IL-2 or IL-15) on the T cell surface was quantitatively determined and the corresponding growth response metrics were calculated over a range of IL-2 and IL-15 concentrations. The integral of cell viability as well as the maximum cell number correlate linearly with the number of interleukin molecules (C125S or IL-15) captured in cell surface receptor reservoirs initially (FIGS. 17A and 17B), for C125S, IL-2 mutants, and IL-15 over all concentrations considered. Thus, the growth versus initial receptor occupancy pharmacodynamic response is quantitatively equivalent for IL-2 mutants and IL-15. IL-2 mutants with increased IL-2Rα affinity provide initial receptor occupancies comparable to IL-15 leading to prolonged cell surface persistence and hence growth response quantitatively equivalent to IL-15.

The growth curves for C125S and the IL-2 mutants were normalized by the maximum viable cell density for each concentration (FIG. 18) and then shifted on the time axis such that the viable cell density extrapolates to zero after at least 14 days (FIG. 19). The value of 14 days was arbitrarily chosen because the viable cell density for T cell cultures treated with 1 nM 2-4 (highest concentration used for the IL-2 mutant with highest IL-2Rα binding affinity) extrapolates to zero after 14 days. We find that the normalization procedure followed by shifting on the time axis collapses the growth curves for C125S and all the IL-2 mutants, at all concentrations, onto one universal growth curve. Normalization by the maximum cell density gives a specific growth rate at each concentration. The existence of a universal growth curve implies that the specific growth rate is independent of concentration. This is consistent with the quantal signal transduction hypothesis for IL-2 induced T cell growth (Smith, *Annu Rev Cell Biol* 5:397-425, 1989). IL-2 mediates the generation of growth signal upon binding the trimeric IL-2Rαβγ receptor. Once this signal exceeds a certain threshold, growth occurs at a specific growth rate independent of the magnitude of the growth signal. Also, in case of an IL-2 (or IL-15) dependent cell line such as F15R-Kit, the absence of a critical amount of growth signal leads to cell death. The magnitude of shift on time axis can be interpreted as the length of time required to attain this threshold value of signal and correlates strongly with initial receptor occupancy (FIG. 20).

As with IL-2, the growth kinetics of IL-15 can also be described by a qualitatively similar universal growth curve (FIG. 21A). T cells treated with 100 pM IL-15 (or greater concentrations) undergo cell death at a slower rate than the IL-2 mutants. This can be explained on the basis of prolonged signaling due to increased persistence of IL-15 relative to any IL-2 mutant. As explained earlier, this increased persistence is most likely due to increased recycling of IL-15 bound to IL-15Rα to the cell surface. The essentially similar universal growth curves for IL-2 and IL-15 further reinforce the functional equivalence of the pharmacodynamic response mediated by high IL-2Rα affinity IL-2 mutants and IL-15. We have established a quantitative relationship between affinity, cell surface persistence, and biological activity for IL-2 and IL-15. Cell surface IL-15Rα acts as a capture reagent for IL-15 that retains IL-15 on the cell surface for a prolonged period of time and mediates growth of T cells expressing IL-15Rα. IL-2Rα acts as a similar cell surface ligand reservoir for IL-2 mutants with increased affinity for IL-2Rα. Similar to IL-15, these IL-2 mutants persist on the cell surface for a prolonged period of time and mediate T cell growth. We have shown that the growth responses mediated by the high IL-2Rα affinity IL-2 mutants and IL-15 are quantitatively equivalent. Our results strongly suggest that the difference in biological activity between wild-type IL-2 and IL-15 in vivo is due to the vastly different affinities of these species for their respective private alpha receptor subunit.

The IL-15-like behavior of high IL-2Rα affinity IL-2 mutants has clear implications for IL-2 based cancer immunotherapy. IL-2 is FDA-approved for the treatment of metastatic renal cell carcinoma and melanoma (Fyfe et al., *J. Clin. Oncol.* 13:688-696, 1995; Atkins et al., *J. Clin. Oncol.* 17:2105-2116, 1999). At nanomolar concentrations, wild-type IL-2 mediates deleterious toxic effects through IL-2βγ on CD56 dim NK cells. The increased potency of high CD25 affinity IL-2 mutants relative to wild-type IL-2 would allow the use of reduced dose concentrations with conceivably lower toxicity. Wild-type IL-2-induced AICD (activation-induced cell death) may cause death of activated T cells recognizing cancer antigens. The use of IL-15 to replace IL-2 in cancer immunotherapy has been suggested due to the inhibitory effects of IL-15 on AICD (Waldmann et al., *Immunity* 14:105-110, 2001). However the broad tissue distribution IL-15Rα would conceivably lead to the undesirable targeting of several different cell types by IL-15 (Fehniger and Caligiuri, *Blood* 97:14-32, 2001). The expression of CD25 (i.e., IL-2Rα) is predominantly restricted to activated T cells. Therefore, high CD25 affinity IL-2 mutants would mediate a biological response functionally equivalent to IL-15 specifically on the desired target cells. Thus, the high CD25 affinity IL-2 mutants combine the specificity of wild-type IL-2 with the beneficial effects of IL-15 and potentially have great therapeutic value.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, although IL-2 is referred to throughout the specification, one of skill in the art would appreciate that the methods and compositions described herein are equally applicable to other cytokines, for example, granulocyte-macrophage colony-stimulating factor (GM-CSF), IL-2, IL-3, IL-5, IL-6, or IL-15 with this property. Thus, the invention also includes mutants of GM-CSF, IL-2, IL-3, IL-5, IL-6, and IL-15 with increased binding affinity for their respective receptors, as compared to wild-type, and methods for identifying and using those mutants.

What is claimed is:

1. A mutant interleukin-2 (IL-2) polypeptide comprising an amino acid sequence set forth in SEQ ID NO: 2 and further comprising one or more amino acid substitutions at positions 69, 74, and 128 of SEQ ID NO: 2, wherein the polypeptide binds an IL-2 receptor alpha subunit (IL-2Rα) with an affinity that is greater than the affinity with which the polypeptide represented by SEQ ID NO: 3 binds to IL-2Rα.

2. The mutant IL-2 polypeptide of claim 1, wherein amino acid residue 69 has been substituted.

3. The mutant IL-2 polypeptide of claim 1, wherein amino acid residue 74 has been substituted.

4. The mutant IL-2 polypeptide of claim 1, wherein amino acid residue 128 has been substituted.

5. The mutant IL-2 polypeptide of claim 1, wherein amino acid residues 69 and 74 have been substituted.

6. The mutant IL-2 polypeptide of claim 1, wherein amino acid residues 69, 74 and 128 have been substituted.

7. The mutant IL-2 polypeptide of claim 1, wherein aside from amino acid substitutions at positions 69, 74, and 128 of SEQ ID NO: 2, the amino acid sequence of the mutant IL-2 polypeptide is otherwise identical to SEQ ID NO: 2.

8. The mutant IL-2 polypeptide of claim 1, further comprising an additional amino acid substitution.

9. The mutant IL-2 polypeptide of claim 1, wherein alanine is substituted for valine at position 69, proline is substituted for glutamine at position 74, and threonine is substituted for isoleucine at position 128.

10. The mutant IL-2 polypeptide of claim 1, wherein the mutant polypeptide binds to the IL-2Rα subunit with a $K_d$ of less than 28 nM.

11. The mutant IL-2 polypeptide of claim 10, wherein the mutant IL-2 polypeptide binds to the IL-2α subunit with a $K_d$ of equal to or less than about 25 nM.

12. The mutant IL-2 polypeptide of claim 11, wherein the mutant IL-2 polypeptide binds to the IL-2R.alpha,

```
                          SEQUENCE LISTING

<160> NUMBER OF SEQ ID NOS: 24

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

-continued

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 3
<211> LENGTH: 132
<212> TYPE: PRT
<213> ORGANISM: Homo sapiens

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 4
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Cys Gln Ser Ile
        115                 120                 125

Ile Ser Thr Leu Thr
        130

<210> SEQ ID NO 5
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 5

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 6
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 6

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Arg
 50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

```
<210> SEQ ID NO 7
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 7

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Ala Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 8
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 8

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Thr
        115                 120                 125

Ile Ser Thr Leu Thr
        130

<210> SEQ ID NO 9
<211> LENGTH: 133
<212> TYPE: PRT
<213> ORGANISM: Artificial Sequence
```

```
<220> FEATURE:
<223> OTHER INFORMATION: Mutation from IL-2

<400> SEQUENCE: 9

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Ala Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Asn
        130

<210> SEQ ID NO 10
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 10

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asp Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Ser Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 11

Ala Pro Thr Ser Ser Ser Thr Lys Lys Thr Gln Leu Gln Leu Glu His
```

```
                1               5                  10                 15
Leu Leu Leu Asp Leu Gln Met Ile Leu Asn Gly Ile Asn Asn Tyr Lys
                20                 25                 30

Asn Pro Lys Leu Thr Arg Met Leu Thr Phe Lys Phe Tyr Met Pro Lys
                35                 40                 45

Glu Ala Thr Glu Leu Lys His Leu Gln Cys Leu Glu Glu Leu Lys
    50                 55                 60

Pro Leu Glu Glu Ala Leu Asn Leu Val Gln Ser Glu Asn Phe His Leu
 65                70                 75                 80

Arg Pro Arg Asp Leu Ile Ser Asn Ile Asn Val Ile Val Leu Glu Leu
                85                 90                 95

Lys Gly Ser Glu Thr Thr Phe Met Cys Glu Tyr Ala Asp Glu Thr Ala
                100                105                110

Thr Ile Val Glu Phe Leu Asn Arg Trp Ile Thr Phe Cys Gln Ser Ile
                115                120                125

Ile Ser Thr Leu Thr
            130

<210> SEQ ID NO 12
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 12

Ala Pro Thr Ser Ser Ser Thr Lys Lys Thr Gln Leu Gln Leu Glu His
 1               5                 10                 15

Leu Leu Leu Asp Leu Gln Met Ile Leu Asn Gly Ile Asn Ser Tyr Lys
                20                 25                 30

Asn Pro Lys Leu Thr Arg Met Leu Thr Phe Lys Phe Tyr Met Pro Lys
                35                 40                 45

Lys Ala Thr Glu Leu Lys His Leu Gln Cys Leu Glu Glu Leu Lys
    50                 55                 60

Pro Leu Glu Glu Ala Leu Asn Leu Ala Pro Ser Lys Asn Phe His Leu
 65                70                 75                 80

Arg Pro Arg Asp Leu Ile Ser Asn Ile Asn Val Ile Val Leu Glu Leu
                85                 90                 95

Lys Gly Ser Glu Thr Thr Phe Met Cys Glu Tyr Ala Asp Glu Thr Ala
                100                105                110

Thr Ile Val Glu Phe Leu Asn Arg Trp Ile Thr Phe Cys Gln Ser Ala
                115                120                125

Ile Ser Thr Leu Thr
            130

<210> SEQ ID NO 13
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 13

Ala Pro Thr Ser Ser Ser Thr Lys Lys Thr Gln Leu Gln Leu Glu His
 1               5                 10                 15

Leu Leu Leu Asp Leu Gln Met Ile Leu Asn Gly Ile Asn Asn Tyr Lys
                20                 25                 30

Asn Pro Lys Leu Thr Arg Met Leu Thr Phe Lys Phe Tyr Met Pro Lys
```

```
                35                  40                  45
Lys Ala Thr Glu Leu Lys His Leu Gln Cys Leu Glu Glu Leu Lys
 50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Pro Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 14
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 14

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Ser Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Leu Lys
 50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Thr
        115                 120                 125

Ile Ser Thr Leu Thr
        130

<210> SEQ ID NO 15
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 15

Ala Pro Thr Ser Ser Ser Thr Lys Thr Thr Arg Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Arg Leu Thr Arg Met Leu Thr Phe Lys Phe Tyr Met Pro Lys
         35                  40                  45

Lys Ala Thr Glu Leu Lys His Leu Gln Cys Leu Glu Glu Leu Lys
 50                  55                  60

Pro Leu Glu Glu Ala Leu Asn Leu Ala Pro Ser Lys Asn Phe His Leu
```

```
                65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130

<210> SEQ ID NO 16
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 16

Thr Pro Thr Ser Ser Thr Lys Lys Thr Gln Leu Gln Leu Glu His
  1               5                  10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Leu Pro Lys
                35                  40                  45
Arg Ala Thr Glu Leu Lys His Leu Gln Cys Leu Glu Asp Glu Leu Lys
        50                  55                  60
Pro Leu Glu Glu Ala Leu Asn Leu Ala Gln Ser Lys Asn Phe Arg Leu
65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130

<210> SEQ ID NO 17
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 17

Ala Pro Thr Ser Ser Thr Lys Lys Thr Gln Leu Gln Leu Glu His
  1               5                  10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Glu
                35                  40                  45
Lys Ala Thr Glu Leu Lys His Leu Gln Cys Leu Glu Glu Glu Leu Lys
        50                  55                  60
Pro Leu Glu Asp Val Leu Thr Leu Ala Gln Ser Lys Asn Phe His Leu
65                  70                  75                  80
Arg Pro Arg Asp Leu Ile Ser Asn Ile His Val Ile Val Leu Glu Leu
                    85                  90                  95
Lys Gly Ser Glu Thr Thr Ser Met Cys Glu Tyr Ala Asp Glu Thr Ala
```

```
                      100                 105                 110

Thr Val Val Glu Phe Leu Asn Arg Trp Ile Thr Phe Cys Gln Ser Ile
        115                 120                 125

Ile Ser Thr Leu Thr
        130

<210> SEQ ID NO 18
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 18

Ala Pro Thr Pro Ser Ser Thr Lys Lys Ala Arg Leu Gln Leu Glu His
  1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Ala
        130

<210> SEQ ID NO 19
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 19

Ala Pro Thr Ser Ser Ser Thr Lys Lys Thr Gln Leu Gln Leu Lys His
  1               5                  10                  15

Leu Leu Leu Asp Leu Gln Met Ile Leu Asn Gly Ile Asn Ser His Lys
             20                  25                  30

Asn Pro Arg Leu Thr Arg Met Leu Thr Phe Lys Phe Tyr Met Pro Glu
         35                  40                  45

Lys Ala Thr Glu Leu Lys His Leu Gln Cys Leu Glu Glu Glu Leu Lys
     50                  55                  60

Pro Leu Glu Glu Ala Leu Asn Leu Ala Pro Ser Lys Asn Phe His Leu
 65                  70                  75                  80

Arg Pro Arg Asp Leu Ile Ser Asn Ile Asn Val Thr Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
```

<210> SEQ ID NO 20
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 20

```
Ala Pro Thr Ser Ser Ser Thr Lys Lys Thr Gln Leu Gln Leu Glu His
 1               5                  10                  15
Leu Leu Leu Asp Leu Gln Met Ile Leu Asn Gly Ile Asn Ser Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Asp Ala Leu Ala Leu Ala Pro Arg Asn Phe His Leu
65                  70                  75                  80
Arg Pro Arg Asp Leu Ile Ser Asn Ile His Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130
```

<210> SEQ ID NO 21
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 21

```
Ala Pro Thr Ser Ser Ser Thr Lys Lys Thr Gln Leu Gln Leu Glu His
 1               5                  10                  15
Leu Leu Leu Asp Leu Gln Met Ile Leu Asn Gly Ile Asn Ser Cys Lys
            20                  25                  30
Asn Pro Lys Leu Ala Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Ala Leu Asn Leu Val Pro Ser Lys Asn Phe Arg Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Thr
        115                 120                 125
Ile Ser Thr Leu Thr
        130
```

<210> SEQ ID NO 22
<211> LENGTH: 133
<212> TYPE: PRT

```
<213> ORGANISM: Artificial Sequence
<220> FEATURE:
<223> OTHER INFORMATION: Mutation from IL-2

<400> SEQUENCE: 22

Ala Pro Thr Ser Ser Ser Thr Lys Lys Thr Gln Leu Gln Leu Glu His
 1               5                  10                  15

Leu Leu Leu Asp Leu Gln Met Ile Leu Asp Gly Ile Ser Ser Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Arg His Leu Gln Cys Leu Glu Glu Glu Leu Lys
    50                  55                  60

Pro Leu Gly Glu Ala Leu Asn Leu Ala Pro Ser Lys Asn Phe His Leu
65                  70                  75                  80

Arg Pro Arg Asp Leu Ile Ser Asn Ile Asn Val Thr Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 23
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 23

Ala Pro Thr Ser Ser Ser Thr Arg Lys Thr Gln Leu Arg Leu Glu His
 1               5                  10                  15

Leu Leu Leu Asp Leu Gln Met Ile Leu Asp Gly Ile Asn Thr Tyr Lys
            20                  25                  30

Asn Pro Arg Leu Arg Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Thr Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 24
<211> LENGTH: 133
<212> TYPE: PRT
<213> ORGANISM: Artificial Sequence
<220> FEATURE:
<223> OTHER INFORMATION: Mutation from IL-2

<400> SEQUENCE: 24
```

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Ser Asn His Lys
            20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
    50                  55                      60

Pro Leu Glu Glu Ala Leu Arg Leu Ala Pro Ser Lys Asn Phe His Leu
65                  70                  75                  80

Arg Pro Arg Asp Leu Ile Ser Asp Val Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```